US011690559B2

(12) United States Patent
Annoni et al.

(10) Patent No.: US 11,690,559 B2
(45) Date of Patent: *Jul. 4, 2023

(54) METHOD AND APPARATUS FOR MONITORING RESPIRATORY DISTRESS BASED ON AUTONOMIC IMBALANCE

(71) Applicant: Cardiac Pacemakers, Inc., St. Paul, MN (US)

(72) Inventors: Elizabeth Mary Annoni, White Bear Lake, MN (US); Viktoria A. Averina, Shoreview, MN (US); Jeffrey E. Stahmann, Ramsey, MN (US); Bryan Allen Clark, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1190 days.

This patent is subject to a terminal disclaimer.

(21) Appl. No.: 16/184,072

(22) Filed: Nov. 8, 2018

(65) Prior Publication Data

US 2019/0167176 A1 Jun. 6, 2019

Related U.S. Application Data

(60) Provisional application No. 62/595,174, filed on Dec. 6, 2017.

(51) Int. Cl.
*A61B 5/00* (2006.01)
*A61B 5/0205* (2006.01)
(Continued)

(52) U.S. Cl.
CPC .......... *A61B 5/4035* (2013.01); *A61B 5/0205* (2013.01); *A61B 5/02405* (2013.01);
(Continued)

(58) Field of Classification Search
CPC ........................... A61B 5/4035; A61B 5/4836
(Continued)

(56) References Cited

U.S. PATENT DOCUMENTS 6,015,388 A 1/2000 Sackner et al.
6,129,675 A 10/2000 Jay
(Continued)

FOREIGN PATENT DOCUMENTS

EP 3171768 B1 9/2020
WO WO-WO2016019250 2/2016

OTHER PUBLICATIONS

"Asthma", CDC website for Asthma: https://www.cdc.gov/nchs/fastats/asthma.htm, Mar. 31, 2017, (3 pps.).
(Continued)

*Primary Examiner* — Nicole F Lavert
(74) *Attorney, Agent, or Firm* — Schwegman Lundberg & Woessner, P.A.

(57) ABSTRACT

An example of a system for monitoring and treating respiratory distress in a patient may include signal inputs, a signal processing circuit, and a respiratory distress analyzer. The signal inputs may be configured to receive patient condition signals indicative of autonomic balance of the patient. The signal processing circuit may be configured to process the patient condition signals and to generate patient condition parameters indicative of the autonomic balance using the processed patient condition signals. The respiratory distress analyzer may be configured to determine a state of the respiratory distress using the patient condition parameters, and may include a parameter analysis circuit configured to analyze the autonomic balance of the patient and to determine the state of the respiratory distress using an outcome of the analysis.

20 Claims, 13 Drawing Sheets

(51) Int. Cl.

| | | |
|---|---|---|
| *A61B 7/00* | (2006.01) | |
| *A61B 5/08* | (2006.01) | |
| *A61B 5/024* | (2006.01) | |
| *A61B 5/352* | (2021.01) | |
| *A61B 5/085* | (2006.01) | |
| *A61B 5/021* | (2006.01) | |
| *A61B 5/11* | (2006.01) | |
| *A61B 5/113* | (2006.01) | |
| *A61B 5/318* | (2021.01) | |

(52) U.S. Cl.
CPC ............ *A61B 5/0823* (2013.01); *A61B 5/352* (2021.01); *A61B 5/4836* (2013.01); *A61B 5/7275* (2013.01); *A61B 5/7278* (2013.01); *A61B 5/746* (2013.01); *A61B 7/003* (2013.01); *A61B 5/0022* (2013.01); *A61B 5/0024* (2013.01); *A61B 5/021* (2013.01); *A61B 5/02416* (2013.01); *A61B 5/085* (2013.01); *A61B 5/0816* (2013.01); *A61B 5/1116* (2013.01); *A61B 5/1118* (2013.01); *A61B 5/1135* (2013.01); *A61B 5/318* (2021.01); *A61B 5/4806* (2013.01)

(58) Field of Classification Search
USPC .......................................................... 604/66
See application file for complete search history.

(56) References Cited

U.S. PATENT DOCUMENTS

| | | |
|---|---|---|
| 7,077,810 B2 | 7/2006 | Lange et al. |
| 7,160,252 B2 | 1/2007 | Cho et al. |
| 7,186,220 B2 | 3/2007 | Stahmann et al. |
| 7,575,553 B2 | 8/2009 | Stahmann et al. |
| 7,678,061 B2 | 3/2010 | Lee et al. |
| 7,690,378 B1 | 4/2010 | Turcott |
| 8,065,001 B1 | 11/2011 | Nabutovsky et al. |
| 8,323,204 B2 | 12/2012 | Stahmann et al. |
| 8,403,861 B2 | 3/2013 | Williams et al. |
| 8,403,865 B2* | 3/2013 | Halperin ............... A61N 1/3956 600/584 |
| 9,066,659 B2 | 6/2015 | Thakur et al. |
| 2004/0116784 A1 | 6/2004 | Gavish |
| 2004/0249416 A1* | 12/2004 | Yun .................... A61N 1/36189 607/2 |
| 2005/0036943 A1* | 2/2005 | Broughton ........... A61K 31/221 424/9.1 |
| 2005/0240241 A1* | 10/2005 | Yun ....................... A61N 1/326 607/42 |
| 2006/0100666 A1 | 5/2006 | Wilkinson et al. |
| 2007/0048180 A1 | 3/2007 | Gabriel et al. |
| 2008/0269625 A1* | 10/2008 | Halperin ................ A61B 5/746 600/534 |
| 2010/0275921 A1 | 11/2010 | Schindhelm et al. |
| 2012/0116241 A1 | 5/2012 | Shieh et al. |
| 2012/0303079 A1* | 11/2012 | Mahajan ............ A61N 1/36564 607/17 |
| 2013/0018595 A1 | 1/2013 | Atakhorrami et al. |
| 2013/0310699 A1 | 11/2013 | Hart et al. |
| 2014/0277278 A1* | 9/2014 | Keel .................. A61N 1/36114 607/59 |
| 2015/0148699 A1 | 5/2015 | Wariar et al. |
| 2016/0224750 A1 | 8/2016 | Kethman et al. |
| 2017/0161453 A1 | 6/2017 | Stahmann et al. |
| 2017/0347968 A1 | 12/2017 | Maile et al. |
| 2017/0347969 A1 | 12/2017 | Thakur et al. |
| 2018/0055564 A1 | 3/2018 | Clark et al. |
| 2018/0056074 A1 | 3/2018 | Clark et al. |
| 2019/0167209 A1 | 6/2019 | Annoni et al. |

OTHER PUBLICATIONS

"Asthma: Could your childhood asthma recur?", https://www.healthxchange.sg/asthma/essential-guide-asthma/childhood-asthma-recur, Nov. 6, 2018, 5 pgs.

"Chronic Obstructive Pulmonary Disease (COPD) Includes: Chronic Bronchitis and Emphysema", CDC website for COPD: https://www.cdc.gov/nchs/fastats/copd.htm, Nov. 6, 2018, 3 pps.

Devi, TH Pricila, et al., "A study of the sympathetic nervous system in bronchial asthma", Journal of Medical Society / Sep.-Dec. 2012 / vol. 26 | Issue 3.

Dinakar, Chitra, "Management of acute loss of asthma control in the yellow zone: a practice parameter", Ann Allergy Asthma Immunol 113 (2014) 143-159.

Emin, Ozkaya, et al., "Autonomic dysfunction and clinical severity of disease in children with allergic rhinitis", International Journal of Pediatric Otorhinolaryngology 76 (2012) 1196-1200.

Gouveia, S., et al., "Assessing Baroreflex Sensitivity in the Sequences Technique: Local versus Global Approach", Computers in Cardiology 2005;32:279-282.

Hayano, Junichiro, et al., "Hypothesis: respiratory sinus arrhythmia is an intrinsic resting function of cardiopulmonary system", Cardiovascular Research 58 (2003) 1-9.

Heffernan, K.S., et al., "Arterial Stiffness and Baroreflex Sensitivity Following Bouts of Aerobic and Resistance Exercise", Int J Sports Med 2007; 28: 197-203.

Jartti, Tuomas T., et al., "Altered cardiovascular autonomic regulation after salmeterol treatment in asthmatic children", Clinical Physiology 18, 4, 345-353 © 1998 Blackwell Science Ltd.

Jartti, Tuomas, et al., "The acute effects of inhaled salbutamol on the beat-to-beat variability of heart rate and blood pressure assessed by spectral analysis", Br J Clin Pharmacol 1997; 43: 421-428.

Kallenbach, J.M, et al., "Reflex Heart Rate Control in Asthma* Evidence of Parasympathetic Overactivity", Chest 1985;87;644-648.

Lewis, M.J., et al., "Autonomic nervous system control of the cardiovascular and respiratory systems in asthma", Respiratory Medicine (2006) 100, 1688-1705.

Ogoh, Shigehiko, et al., "Autonomic nervous system influence on arterial baroreflex control of heart rate during exercise in humans", J Physiol 566.2 (2005) pp. 599-611.

Papiris, Spyros, et al., "Clinical review: Severe asthma", Critical Care, Feb. 2002, 6:1, 30-44.

Parlow, Joel, et al., "Comparison With Drug-Induced Responses", Hypertension May 1995, vol. 25, Issue 5, https://www.ahajournals.org/doi/full/10.1161/01.HYP.25.5.1058, 17 pgs.

Partridge, Martyn R., et al., "Attitudes and actions of asthma patients on regular maintenance therapy: the INSPIRE study", BMC Pulmonary Medicine 2006, 6:13, 9 pgs.

Patakas, D., et al., "Reduced baroreceptor sensitivity in patients with chronic obstructive pulmonary disease", thorax 1982 ;37 :292-295.

Reis, Michel Silva, et al., "Deep Breathing Heart Rate Variability is Associated With Respiratory Muscle Weakness in Patients With Chronic Obstructive Pulmonary Disease", Clinics 2010;65(4):369-75.

Seemungal, Terence, et al., "Respiratory Viruses, Symptoms, and Inflammatory Markers in Acute Exacerbations and Stable Chronic Obstructive Pulmonary Disease", Am J Respir Crit Care Med vol. 164. pp. 1618-1623, 2001.

Sherwood, Greg, et al., "Systems and Methods for Assessing the Health Status of a Patient", U.S. Appl. No. 15/982,506, filed May 17, 2018.

Swenne, C. A., "Baroreflex sensitivity: mechanisms and measurement", Neth Heart J 21, (2013), 58-60.

Tattersfield, Anne E., et al., "Exacerbations of Asthma, A Descriptive Study of 425 Severe Exacerbations", Am J Respir Crit Care Med 1999;160:594-599.

Van Den Berge, Maarten, et al., "Prediction and course of symptoms and lung function around an exacerbation in chronic obstructive pulmonary disease", Respiratory Research 2012, 13:44, http://respiratory-research.com/content/13/1/44, 9 pgs.

(56) References Cited

OTHER PUBLICATIONS

Van Gestel, Arnoldus Jr, et al., "Autonomic dysfunction in patients with chronic obstructive pulmonary disease (COPD)", J Thorac Dis 2010; 2: 215-222.

Volterrani, Maurizio, et al., "Decreased Heart Rate Variability in Patients With Chronic Obstructive Pulmonary Disease*", Chest /106 / 5 / Nov. 1994, 1433-1437.

"U.S. Appl. No. 16/184,020, Advisory Action dated Nov. 3, 2021", 3 pgs.

"U.S. Appl. No. 16/184,020, Final Office Action dated Sep. 9, 2021", 15 pgs.

"U.S. Appl. No. 16/184,020, Non Final Office Action dated Mar. 16, 2021", 14 pgs.

"U.S. Appl. No. 16/184,020, Non Final Office Action dated May 11, 2022", 14 pgs.

"U.S. Appl. No. 16/184,020, Response filed Jun. 8, 2021 to Non Final Office Action dated Mar. 16, 2021", 10 pgs.

"U.S. Appl. No. 16/184,020, Response filed Oct. 25, 2021 to Final Office Action dated Sep. 9, 2021", 11 pgs.

"U.S. Appl. No. 16/184,020, Response filed Dec. 22, 2020 to Restriction Requirement dated Oct. 30, 2020", 7 pgs.

"U.S. Appl. No. 16/184,020, Restriction Requirement dated Oct. 30, 2020", 6 pgs.

Narkiewicz, K, et al., "Baroreflex control of sympathetic nerve activity and heart rate in obstructive sleep apnea", Hypertension. 32(6), (Dec. 1998), 1039-43.

"U.S. Appl. No. 16/184,020, Response filed Aug. 10, 2022 to Non Final Office Action dated May 11, 2022", 11 pgs.

\* cited by examiner

METHOD AND APPARATUS FOR MONITORING RESPIRATORY DISTRESS BASED ON AUTONOMIC IMBALANCE

CLAIM OF PRIORITY

This application claims the benefit of priority under 35 U.S.C. § 119(e) of U.S. Provisional Patent Application Ser. No. 62/595,174, filed on Dec. 6, 2017, which is herein incorporated by reference in its entirety.

CROSS REFERENCE TO RELATED APPLICATIONS

This application is related to commonly assigned U.S. Provisional Patent Application Ser. No. 62/595,166, entitled "NON-INVASIVE SYSTEM FOR MONITORING AND TREATING RESPIRATORY DISTRESS", filed on Dec. 6, 2017, which is incorporated by reference in their entirety.

TECHNICAL FIELD

This document relates generally to medical devices and more particularly to a system that monitors a patient for predicting, detecting, and/or treating respiratory distress.

BACKGROUND

Obstructive lung diseases, including chronic obstructive pulmonary disease (COPD) and asthma, are characterized by narrowing airways that can make fully expelling air from the lungs difficult. COPD and asthma patients can experience a significant decline in health (e.g., acute COPD exacerbations and asthma attacks), to extents that require hospitalization. Despite advances in therapeutics, the prevalence of COPD and asthma continues to grow.

COPD currently affects nearly 13 million people in the United States and is the third leading cause of death in the country. The overwhelming primary cause of COPD is inhalation of cigarette smoke, responsible for over 90% of COPD cases. The economic and social burden of the disease is substantial and is increasing. The annual economic burden is currently estimated to be around $32 billion in the United States alone. Conditions associated with COPD include chronic bronchitis and emphysema. Chronic bronchitis is characterized by chronic cough with sputum production. Airway inflammation, mucus hypersecretion, airway hyper-responsiveness, and eventual fibrosis of the airway walls result in significant airflow and gas exchange limitations. Emphysema is characterized by destruction of the lung parenchyma, which leads to a loss of elastic recoil and tethering that maintains airway patency. Because bronchioles are not supported by cartilage like the larger airways are, they have little intrinsic support and therefore are susceptible to collapse when destruction of tethering occurs, particularly during exhalation.

Asthma is similar to chronic bronchitis, though its underlying cause is often an inherent defect of airway smooth muscle or the inflammatory milieu, which makes airway smooth muscle hyperreactive. Chronic asthma can have similar airway wall thickening as in chronic bronchitis, leading to a permanent, irreversible airflow obstruction. Asthma impacts over 18 million adults in the United States. Strikingly, there are 1.6 million visits to the emergency rooms resulting from this disease in the United States annually. Asthma COPD overlap syndrome (ACOS) is a condition in which a patient has clinical features of both asthma and COPD. ACOS patients are often among the sickest and most difficult to treat.

The most significant contributor to the economic burden of these diseases is related to healthcare services for asthma attacks and acute exacerbations of COPD (AECOPD), mostly emergency care and inpatient health care. Despite relatively efficacious drugs that treat COPD symptoms (e.g., long-acting muscarinic antagonists, long-acting beta agonists, corticosteroids, and antibiotics), a particular segment of patients known as "frequent exacerbators" often visit the emergency rooms and hospitals with exacerbations and also have a more rapid decline in lung function, poorer quality of life, and greater mortality. Similarly, a group of severe asthmatics are amongst those who visits the emergency rooms most frequently.

Currently, a successful strategy for managing asthma and COPD is the action plan that follows a "traffic light model" to monitor patient conditions and respond to changes. The traffic light model uses the analogy of traffic lights to illustrate the seriousness of symptoms (with green, yellow, and red zones) and the action a patient must take in each zone. This technique can be used by patients as well as caretakers to monitor symptoms. However, this approach has its limitations. For example, the patient must be compliant and be able to recognize symptoms.

SUMMARY

An example (e.g., "Example 1") of a system for monitoring and treating respiratory distress in a patient may include signal inputs, a signal processing circuit, and a respiratory distress analyzer. The signal inputs may be configured to receive patient condition signals indicative of autonomic balance of the patient. The signal processing circuit may be configured to process the patient condition signals and to generate patient condition parameters using the processed patient condition signals. The patient condition parameters may be indicative of the autonomic balance of the patient. The respiratory distress analyzer may be configured to determine a state of the respiratory distress using the patient condition parameters. The respiratory distress analyzer may include a parameter analysis circuit, which may be configured to analyze the autonomic balance of the patient and to determine the state of the respiratory distress using an outcome of the analysis.

In Example 2, the subject matter of Example 1 may optionally be configured to further include a therapy device configured to deliver one or more therapies treating the respiratory distress and a control circuit configured to control the delivery of the one or more therapies based on the state of the respiratory distress.

In Example 3, the subject matter of any one or any combination of Examples 1 and 2 may optionally be configured to further include a storage device configured to store the state of the respiratory distress determined over time, and may optionally be configured such that the parameter analysis circuit is configured to produce and analyze a trend of the state of the respiratory distress.

In Example 4, the subject matter of any one or any combination of Examples 1 to 3 may optionally be configured such that the parameter analysis circuit is configured to determine a patient condition metric being a linear or nonlinear combination of the patient condition parameters and to produce one or more respiratory distress indicators indicating the state of the respiratory distress based on the patient condition metric, and the respiratory distress analyzer further includes a notification circuit configured to present the one or more respiratory distress indicators.

In Example 5, the subject matter of Example 4 may optionally be configured such that the parameter analysis circuit is configured to perform at least one of prediction or detection of an exacerbation of the respiratory distress based on the patient condition metric, and the notification circuit is configured to produce an alert notifying a result of the performance of the at least one of prediction or detection of the exacerbation.

In Example 6, the subject matter of Example 5 may optionally be configured such that the signal processing circuit is configured to generate patient condition parameters indicative of one or more physiological markers of asthma, the parameter analysis circuit is configured to perform at least one of prediction or detection of an asthma attack, and the notification circuit is configured to produce an asthma alert notifying at least one of the asthma attack being predicted or the asthma attack being detected.

In Example 7, the subject matter of any one or any combination of Examples 5 and 6 may optionally be configured such that the signal processing circuit is configured to generate patient condition parameters indicative of one or more physiological markers of chronic obstructive pulmonary disease (COPD), the parameter analysis circuit is configured to perform at least one of prediction or detection of an exacerbation of COPD, and the notification circuit is configured to produce a COPD alert notifying at least one of the exacerbation of COPD being predicted or the exacerbation of COPD being detected.

In Example 8, the subject matter of any one or any combination of Examples 1 to 7 may optionally be configured to further include a signal processing controller and a signal processing sensor. The signal processing controller is configured to receive a processing control signal and adjust the processing of the patient condition signals based on the processing control signal. The signal processing sensor is configured to sense a physical state of the patient and to produce the processing control signal based on the physical state.

In Example 9, the subject matter of Example 8 may optionally be configured such that the signal processing sensor includes one or more of an activity sensor configured to sense an activity level of the patient or a sleep sensor configured to sense whether the patient is sleeping.

In Example 10, the subject matter of any one or any combination of Examples 1 to 9 may optionally be configured such that the signal inputs are configured to receive one or more respiratory signals indicative of respiratory cycles including inspiratory and expiratory phases and one or more cardiac signals indicative of cardiac cycles including at least ventricular depolarizations, the signal processing circuit is configured to process the one or more respiratory signals and the one or more cardiac signals and to generate one or more respiration-mediated physiological parameters of the patient condition parameters, and the parameter analysis circuit is configured to determine the state of the respiratory distress based on at least the one or more respiration-mediated physiological parameters.

In Example 11, the subject matter of Example 10 may optionally be configured such that the signal processing circuit is configured to generate one or more respiration sinus arrhythmia (RSA) parameters of the one or more respiration-mediated physiological parameters, the one or more RSA parameters being one or more measures of the RSA, and the parameter analysis circuit is configured to determine the state of the respiratory distress based on at least the one or more RSA parameters.

In Example 12, the subject matter of any one or any combination of Examples 1 to 11 may optionally be configured such that the signal inputs are configured to receive one or more blood pressure signals indicative of blood pressure, one or more cardiac signals indicative of cardiac cycles including at least ventricular depolarizations and one or more physical state signals indicative of a physical state of the patient, the signal processing circuit is configured to process the one or more blood pressure signals, the one or more cardiac signals, and the one or more physical state signals and to generate one or more baroreflex sensitivity (BRS) parameters of the patient condition parameters, the one or more BRS parameters being one or more measures of the BRS, and the parameter analysis circuit is configured to determine the state of the respiratory distress based on at least the one or more BRS parameters.

In Example 13, the subject matter of Example 12 may optionally be configured such that the signal processing circuit is configured to generate detect levels of physical activity or exertion of the patient from the one or more physical state signals and to generate the one or more BRS parameters each for a plurality of levels of the physical activity or exertion.

In Example 14, the subject matter of any one or any combination of Examples 12 and 13 may optionally be configured such that the signal processing circuit is configured to generate detect a type of posture change of the patient from the one or more physical state signals and to stratify the one or more BRS parameters by the detected type of posture change.

In Example 15, the subject matter of any one or any combination of Examples 12 to 14 may optionally be configured such that the signal processing circuit is configured to generate detect one or more of a magnitude or a duration of posture change of the patient from the one or more physical state signals and to stratify the one or more BRS parameters by the detected one or more of the magnitude or the duration of posture change.

An example (e.g., "Example 16") of a method for monitoring and treating respiratory distress in a patient is also provided. The method may include receiving patient condition signals indicative of autonomic balance of the patient and monitoring the state of the respiratory distress automatically using a respiratory distress monitoring circuit. The monitoring may include processing the patient condition signals, generating patient condition parameters using the processed patient condition signals, the patient condition parameters indicative of the autonomic balance of the patient, analyzing the autonomic balance of the patient using the patient condition parameters, and determining the state of the respiratory distress using an outcome of the analysis.

In Example 17, the subject matter of Example 16 may optionally further include delivering one or more therapies treating the respiratory distress and controlling the delivery of the one or more therapies based on the state of the respiratory distress.

In Example 18, the subject matter of any one or any combination of Examples 16 and 17 may optionally further include determining a patient condition metric being a linear or nonlinear combination of the patient condition parameters, performing at least one of prediction or detection of an exacerbation of the respiratory distress based on the patient condition metric, and producing an alert notifying a result of the performance of the at least one of prediction and detection.

In Example 19, the subject matter of any one or any combination of Examples 16 to 18 may optionally further include sensing a physical state of the patient and adjusting the processing of the patient condition signals based on the sensed physical state.

In Example 20, the subject matter of receiving patient condition signals as found in any one or any combination of Examples 16 to 19 may optionally further include receiving one or more respiratory signals indicative of respiratory cycles including inspiratory and expiratory phases and one or more cardiac signals indicative of cardiac cycles including at least ventricular depolarizations, and the subject matter of generating the patient condition parameters as found in any one or any combination of Examples 16 to 19 may optionally further include generating one or more respiration-mediated physiological parameters of the patient condition parameters.

In Example 21, the subject matter of generating the one or more respiration-mediated physiological parameters as found in claim 20 may optionally further include generating one or more respiration sinus arrhythmia (RSA) parameters being one or more measures of the RSA.

In Example 22, the subject matter of receiving patient condition signals as found in any one or any combination of Examples 16 to 21 may optionally further include receiving one or more blood pressure signals indicative of blood pressure, one or more cardiac signals indicative of cardiac cycles including at least ventricular depolarizations, and one or more physical state signals indicative of a physical state of the patient, and the subject matter of generating the patient condition parameters as found in any one or any combination of Examples 16 to 21 may optionally further include generating one or more baroreflex sensitivity (BRS) parameters being one or more measures of the BRS.

In Example 23, the subject matter of generating the patient condition parameters as found in claim 22 may optionally further include one or more of: detecting levels of physical activity or exertion of the patient from the one or more physical state signals and generating the one or more BRS parameters each for a plurality of levels of the physical activity or exertion, detecting a type of posture change of the patient from the one or more physical state signals and stratifying the one or more BRS parameters by the detected type of posture change, detecting a magnitude or a duration of posture change of the patient from the one or more physical state signals and stratifying the one or more BRS parameters by the detected magnitude of posture change, or detecting a duration of posture change of the patient from the one or more physical state signals and stratifying the one or more BRS parameters by the detected duration of posture change.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
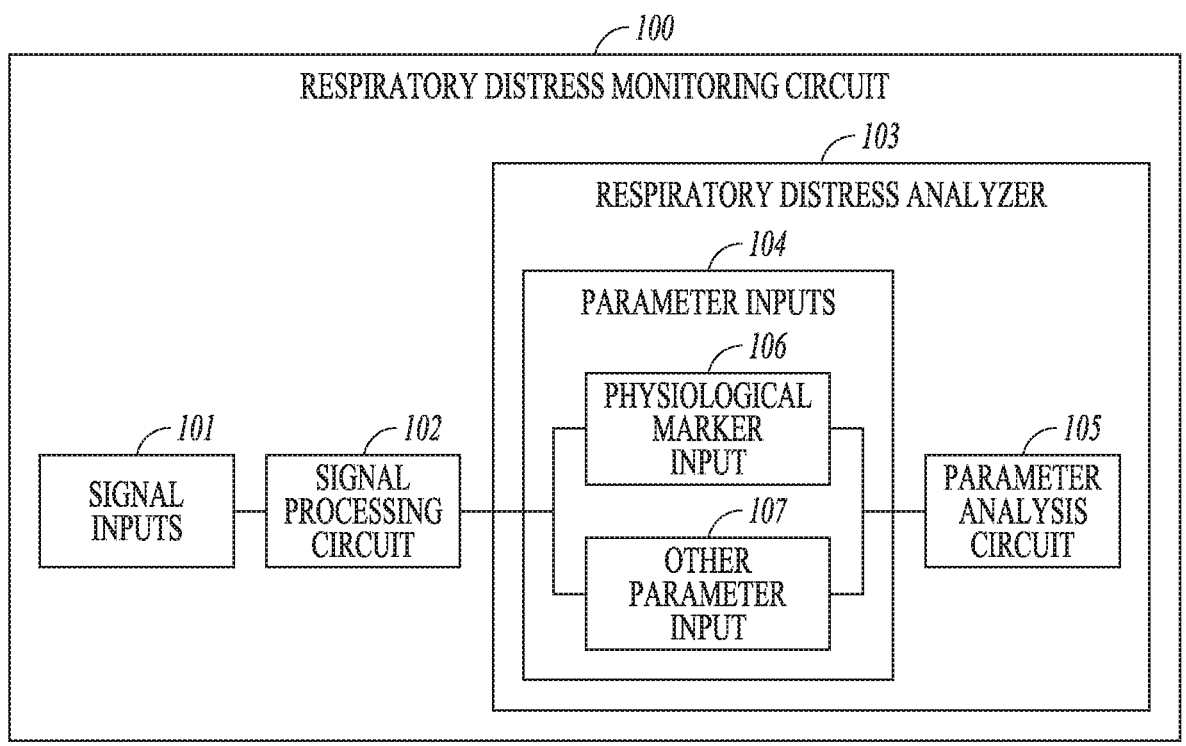
FIG. 1 illustrates an embodiment of a circuit for monitoring respiratory distress of a patient.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, systems and methods for monitoring respiratory distress, including detection and/or prediction of exacerbations of pulmonary diseases affecting airways, such as asthma and chronic obstructive pulmonary disease (COPD). Exacerbations of such diseases create significant economic burden on the healthcare system. Patients experiencing these episodes tend to deteriorate over time. Thus, there is a need for consistent and accurate means to monitor patient status and detect worsening systems prior to an episode requiring hospitalization.

Studies have shown variable durations of increased signs and/or symptoms leading up to exacerbations in asthma patients. However, there are noticeable trends in signs and/or symptoms on average approximately one week prior to the episode. One study found that patients (at least 16 years old, from 11 countries, structured interviews of 3415 adults) reported a mean time from the first appearance to peak of signs and symptoms of 5.1 days (range: <30 minutes to >2 weeks) and a mean interval from the peak of symptoms to recovery of 6.2 days. Another study found that the mean maximal decrease in the morning PEF was 16% to 20%. This decrease was gradual, from day-10 to day-3, followed by a more rapid decrease. It is believed that fast onset episodes are due to triggers such as allergens and irritants, while slow onset episodes are due to faults in management. Analysis of fatal asthma attacks showed that 80% of them had slow onset.

Similar to asthma patients, COPD patients generally have a slow onset of signs and/or symptoms which has been reported to be approximately 1-2 weeks in duration, with symptoms steadily increased from 2 weeks prior to exacerbation, with a sharp rise during the last week. Respiratory tract infection is one of the most common triggers for COPD exacerbation, accounting for a majority of exacerbations.

There is a need for effective monitoring of patients to provide a reliable indication of their conditions and monitor respiratory distress to (1) warn the patients and provide a window to administer therapy to prevent hospitalizations, and/or (2) to alert patients and appropriate medical personnel of the onset of an exacerbation to get the patient the appropriate medical care. There is a need for reducing occurrence of events such as asthma attacks and acute exacerbations of COPD (AECOPD) for these patients, as such events are the primary contributor to the economic and social burden of respiratory diseases.

Failure to provide the correct type and/or duration of therapy for an asthma attack or acute exacerbation of COPD can prevent recovery, delay recovery, or result in an additional asthma attack or acute exacerbation of COPD soon after the initial disease event. Hence there is a need to monitor treatment of patients during recovery from an asthma attack and acute exacerbation of COPD. In one example, there is a need to monitor patients during hospitalization and emergency room visits for asthma attack and acute exacerbation of COPD to ensure the recovery therapy is effective and to prevent premature discharge. In another example, there is a need to monitor patients during recovery away from a hospital setting (e.g., at-home, or nursing home) to ensure compliance and effectiveness of the recovery therapy. Monitoring during recovery may be different from or the same as monitoring apart from recovery. Monitoring during recovery may include more frequent data gathering, gathering of additional or different parameters, and/or more frequent reporting to a caregiver (e.g., medical professional, or at-home caregiver).

As a patient's signs and/or symptoms worsen preceding an exacerbation, non-invasive devices can be used to capture symptomatic and physiological changes to warn the patient of declining health and/or alert appropriate personnel in the event of an exacerbation episode. Signs associated with airway obstruction such as coughing, wheezing (lung sounds), increased respiration rate, and lung hyperinflation can be captured by monitoring the patient using a system of non-invasive sensors. In addition, measures of autonomic activity can be monitored over time to assess patient condition and send a warning for a likely exacerbation based on signals acquired and/or alert appropriate personnel in the event of an exacerbation so that the patient can promptly receive medical attention.

In one example, the present subject matter provides a system that includes a noninvasive or minimally invasive system for monitoring COPD and asthma patients to provide a reliable indication of their condition and detect (1) worsening signs and/or symptoms, to warn patients and provide a window to administer therapy to prevent hospitalizations, and/or (2) exacerbations, in the event of rapid onset of signs and/or symptoms, to alert appropriate medical personnel of the onset of an exacerbation to get the patient the appropriate medical care. This system can also identify changes in the patient's condition subsequent to therapy to indicate a need for adjustment or termination of the therapy. In various embodiments, the system can include one or more sensors that can indirectly or directly sense symptoms and/or physiological signals indicative of worsening condition and/or onset of an exacerbation. The system can also contain a processing unit to process incoming signals and extract appropriate signal information. The processing unit can execute an algorithm to process the incoming signals along with stored data (e.g., trend data) to assess the patient's condition. In the event of worsening signs and/or symptoms preceding or at the onset of an exacerbation, the system can notify the patient, caregiver, and/or appropriate medical personnel.

A biomarker of respiratory distress, such as respiration sinus arrhythmia (RSA), can be captured invasively or noninvasively through direct or indirect means to provide an indication of the patient's condition and provide a warning when the condition becomes worse. RSA is a short term measure of heart rate variability (HRV), and is a physiological indicator that may have implications for monitoring pulmonary diseases such as asthma and COPD. RSA can be used to assess cardiac autonomic function, and can represent the transfer function from respiration rate to cardiac cycle length (e.g., time intervals between successive R-waves, the R-R intervals). During inspiration, inhibitory signals decrease vagal nerve activity, resulting in increased heart rate and decreased RSA. Conversely, during expiration, increasing vagus nerve activity results in decreased HR and increased RSA.

Asthma and COPD are associated with impairment in the autonomic balance (coordination between the sympathetic and parasympathetic nervous systems) which can be reflected by monitoring HRV and/or RSA. This imbalance, demonstrated in COPD patients, manifests as an elevation in sympathetic activity and a withdrawal of parasympathetic activity. In studies with asthma patients, the imbalance in the autonomic nervous system results from the hyperactivity of the parasympathetic branch causing bronchial constriction. In addition, the dysfunction or hypoactivity of the sympathetic branch has been tied to the severity of asthma. These alterations in autonomic balance can be monitored for individual patients to see when RSA deviates from a baseline value, either increasing or decreasing. Since this measure is based on the respiratory signal, RSA can continuously be evaluated to provide feedback on the patient's condition that does not require the patient to be performing a specific task or at an in-office assessment. Additional respiration mediated signals could be captured as a surrogate to heart rate including blood pressure, blood flow/perfusion, heart sounds, direct neural recordings, and blood gas ($O_2$ and $CO_2$) concentrations.

In one example, the present subject matter provides a system that can monitor respiration-mediated signals in patients with pulmonary diseases that restrict airflow, such as asthma, COPD, chronic bronchitis, and emphysema. Heart rate responses to respiration can be captured through invasive or non-invasive means to monitor the patient's condition. This system can alert the patient or caretaker of worsening conditions and/or the need for intervention. This system can also identify changes in the patient's condition subsequent to therapy to indicate a need for adjustment or termination of the therapy. In various embodiments, the system can include one or more sensors that can directly or indirectly sense a respiratory signal and another physiological signal modulated by respiration. These signals can be processed to extract period of the respiration cycle including inspiration and expiration phases. The corresponding respiratory periods of the cardiac signal can be processed to extract heart rate and inter-beat intervals (the R-R intervals). An algorithm can be executed to calculate respiration-mediated signal indices and provide a measure of the patient's condition.

Arterial baroreflex (also referred to as baroreceptor reflex) is important for hemodynamic stability and cardioprotection, and is a strong prognostic indicator. The carotid and aortic baroreceptors detect changes in pressure, providing negative feedback to the closed-loop system for regulating blood pressure. In a healthy person, when baroreceptor activation increases due to a blood pressure increase, efferent parasympathetic activity increases to lower blood pressure through slowing the heart rate and causing peripheral vasodilation. Baroreflex sensitivity (BRS), defined as the change in inter-beat interval (IBI) in ms/mmHg, provides an indication of the function of this closed-loop system and can be measured from standard heart rate and blood pressure monitoring techniques.

Asthma and COPD are associated with impairment in the autonomic balance which can be reflected by monitoring BRS, either through spontaneous measures or clinical evaluations. This imbalance, as demonstrated in COPD patients, manifests as an elevation in sympathetic activity and a withdrawal of parasympathetic activity resulting in decreased BRS. In studies with asthma patients, the imbalance in the autonomic nervous system results from the hyperactivity of the parasympathetic branch. Treatment has been shown to decrease BRS as the cardiovagal responsiveness decrease and sympathetic activity increases. These alterations in autonomic balance can be monitored for individual patients to see when BRS deviates from a baseline value, either increasing or decreasing. Since this measure is based on the respiratory signal, BRS can continuously be evaluated to provide feedback on the patient's condition that does not require the patient to be performing a specific task or at an in-office assessment.

In the event of an AECOPD or asthma attack, the patient has heightened sympathetic nervous system activity, which causes in increase in blood pressure and heart rate. The increased blood pressure in turn activates baroreceptors which down-regulate sympathetic outflow, restoring homeostasis. This baroreflex can increase or decrease blood pressure. In a healthy person who transitions abruptly from a supine to standing position, pooling of blood in the lower extremities causes an immediate arterial blood pressure reduction, which in turn activates baroreceptors to increase sympathetic outflow causing a blood pressure and heart rate increase, again restoring homeostasis. These are healthy compensatory responses. An attenuated baroreceptor response causes a reduced and delayed heart rate and blood pressure response to a posture change (or any physical activity that typically activate the baroreceptors).

Natural BRS response has variability due to respiration, physical and mental stressors, which is evident in everyday activities. These dynamics can be used as an indicator of baroreceptor function, and can be used to monitor patients with airflow limitations. The dynamic BRS response can be captured using beat-to-beat sensitivity to investigate changes in heart rate and blood pressure for each cardiac contraction. One method for measuring BRS is measuring spontaneous BRS. Spontaneous BRS can be measured through consecutive beats that are characterized by simultaneous increases or decreased in blood pressure and R-R interval. BRS is then calculated as the average of the linear regression slopes detected for each sequence over a given time interval. Examples for measuring this dynamic response include measuring through monitoring respiration and/or physical activity.

Similar to respiratory sinus arrhythmia and diminished HRV, diminished BRS is evident in COPD and asthma patients. The dynamic spontaneous BRS can be captured through analysis of blood pressure and heart rate during a respiratory cycle. This is because there is always spontaneous blood pressure variability (BPV) due to respiration. Respiration induces HRV by mediation of the arterial baroreflex and by direct mechanical modulation of the SA node pacemaker properties. Using inspiration and expiration, consecutive increases or decreases can be captured to calculate BRS for monitoring the patient.

Moment-to-moment regulation of blood pressure through the baroreflex is reduced during exercise in comparison to rest. BRS decreases during exercise because the body's operating point on the curve of heart rate against blood pressure has shifted away from the maximal sensitivity point at the center of the curve (at rest condition). The shift moves the "set point" of blood pressure to a higher level with less sensitivity to changes in blood pressure. This change in baroreflex depends on exercise intensity. As the exercise intensity increases (as the heart rate increases), the response curve changes with the lowest sensitivity at the highest exercise intensity where the subjects maintained a heart rate of 150 beat per minute (bpm). As the exercise intensity increases, the operating point progressively moves away from the center point towards the upper threshold of the curve. Pulmonary disease affecting airways such as asthma and COPD are associated with alterations in autonomic function. This dysfunction can be investigated through physical activity by monitoring the baroreflex. Exercise alone causes a decrease in BRS, and exercise compounded with airway limitation may lead to a more significant reduction in BRS. By coupling activity and BRS monitoring, the baroreflex can be evaluated at a higher operating point (due to exercise) for monitoring the patient's condition and evaluating the need for therapeutic intervention.

In one example, the present subject matter provides a system for ambulatory assessment of baroreceptor response. The patient's baroreceptor response to events such as respiration or activity can be used for monitoring the patient's condition related to pulmonary disease, such as asthma and COPD. Heart rate, blood pressure, respiration, and activity signals can be sensed through invasive or non-invasive means, through direct or indirect measures. This system can alert the patient or caretaker of worsening conditions or the need for intervention. This system can also identify changes in the patient's condition subsequent to therapy to indicate a need for adjustment or termination of the therapy. In various embodiments, this system can include an activity sensor, a respiration sensor, and an additional sensor for measuring baroreceptor response. The system can include a processor to process the signals produced by these sensors to analyze the spontaneous baroreceptor response during respiration as detected by the respiration sensor and/or during physical activity as detected by the activity sensor. The processor can execute an algorithm to calculate baroreceptor response indices to provide a measure of the patient's condition.

FIG. 1 illustrates an embodiment of a respiratory distress monitoring circuit 100. Respiratory distress monitoring circuit 100 can include signal inputs 101, a signal processing circuit 102, and a medical condition analyzer 103. In various embodiments, respiratory distress monitoring circuit 100 can be implemented as part of a system for monitoring and/or treating a patient suffering from one or more medical conditions including respiratory distress. Examples of the respiratory distress include COPD and asthma.

Signal inputs 101 can receive patient condition signals indicative of a state of the respiratory distress of the patient. Signal processing circuit 102 can process the patient condition signals and generate patient condition parameters using the processed patient condition signals. The patient condition parameters are indicative of the state of the respiratory distress of the patient. Respiratory distress analyzer 103 can determine the state of the respiratory distress using the patient condition parameters. Respiratory distress analyzer 103 can include parameter inputs 104 and a parameter analysis circuit 105. Parameter inputs 104 can include a physiological marker input 106 to receive one or more physiological marker parameters of the patient condition parameters and an other parameter input 107 to receive one or more other parameters of the patient condition parameters that can be used in the determination of the state of the respiratory distress. The one or more physiological marker parameters represent one of more physiological markers for the respiratory distress and can be one or more quantitative measures of the respiratory distress. Parameter analysis circuit 105 can analyze the patient condition parameters received from signal processing circuit 102 and determine the state of the respiratory distress using an outcome of the analysis.

In one embodiment, the patient condition signals include signals acquired by non-invasive sensors such that respiratory distress monitoring circuit 100 can be used in a non-invasive patient monitoring and/or treatment system. In one embodiment, the patient condition signals include signals indicative of autonomic balance of the patient, and parameter analysis circuit 105 can to analyze the autonomic balance of the patient and determine the state of the respiratory distress based on a state of the autonomic balance. Examples of measures of autonomic balance include RSA and BRS. In one embodiment, parameter analysis circuit 105 can produce a patient condition metric being a linear or nonlinear function of the patient condition parameters and predict an exacerbation of the respiratory distress based on the patient condition metric. Respiratory distress analyzer 103 can produce an alert notifying the prediction of the exacerbation.

Figure 2:
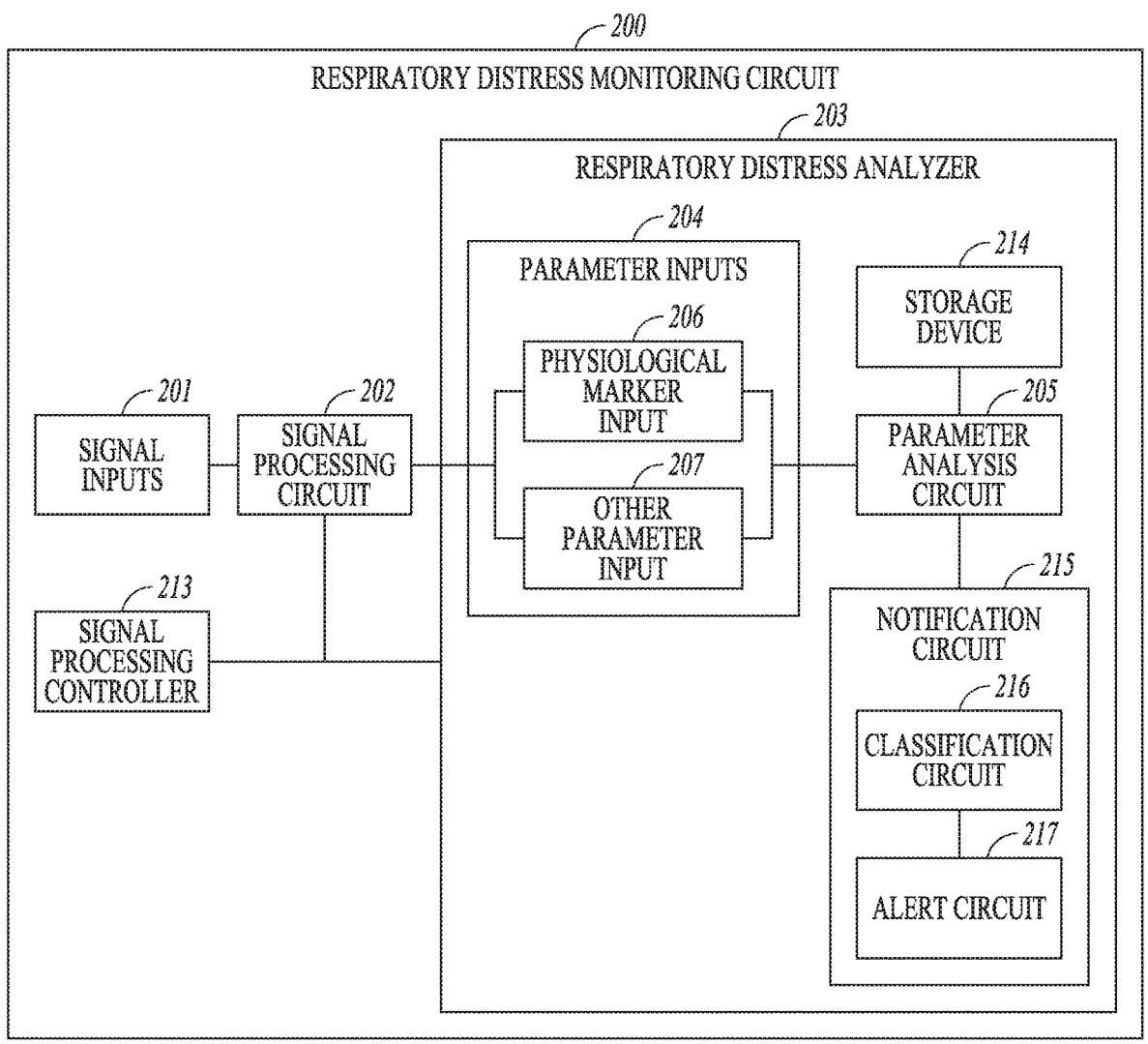
FIG. 2 illustrates an embodiment of another circuit for monitoring respiratory distress of a patient.

FIG. 2 illustrates an embodiment of an embodiment of a respiratory distress monitoring circuit 200, which can represent an example of respiratory distress monitoring circuit 100. Respiratory distress monitoring circuit 200 can include signal inputs 201, a signal processing circuit 202, a signal processing controller 213, and a respiratory distress analyzer 203.

Signal input 201 can represent an example of signal input 101 and can receive the patient condition signals indicative of the state of the respiratory distress. The patient condition signals can include one or more signals sensed by one or more sensors and indicative physiological markers of the respiratory distress and one or more other signals that can otherwise be used by respiratory distress analyzer 203 in determining the state of the respiratory distress. Signal processing circuit 202 can represent an example of signal processing circuit 102 and can process the patient condition signals received by signal inputs 201 and can generate patient condition parameters indicative of the state of the respiratory distress. The patient condition parameters can include one or more physiological marker parameters that are indicative of the physiological markers of the respiratory distress and can allow for detection and/or prediction of exacerbation. In various embodiments, a sensor or a combination of sensors can be employed to monitor symptoms and physiological markers indicative of the state of the respiratory distress. Examples of physiological markers of respiratory distress that can be signs for exacerbation include:

(i) Respiration rate;
  (ii) Lung sounds, including chest sounds that can be examined by tapping chest and using a microphone to capture the response tone;
  (iii) Cough;
  (iv) Wheezing;
  (v) Respiration flow characteristics, such as FEV1, FEV3, FEV6, TC, FVC, MV, TLC, flow rate, volume measures, and any combination of these parameters;
  (vi) Oxygen Saturation;
  (vii) Central cyanosis;
  (viii) Activity levels;
  (ix) Sleep quality;
  (x) Body temperature;
  (xi) Heart rate;
  (xii) Heart rate variability (HRV), including heart rate acceleration and deceleration capacity;
  (xiii) Respiration sinus arrhythmia (RSA);
  (xiv) Blood pressure;
  (xv) Blood pressure variability;
  (xvi) Baroreceptor reflex sensitivity (BRS);
  (xvii) Galvanic skin response;
  (xviii) Direct neural measures including neural respiratory drive index (NRDI), parasternal EMG, diaphragm EMG; and
  (xix) Chemical indicators of stress and inflammation.

In various embodiments, the one or more physiological marker parameters can each indicate and/or be a measure of one or more of these physiological markers. Table 1 includes a more complete list of such physiological markers with rationale for each marker.

Respiratory distress analyzer 203 can represent an example of respiratory distress analyzer 103 and can analyze the patient condition parameters generated by signal processing circuit 202 and determine the state of the respiratory distress based on an outcome of the analysis. Respiratory distress analyzer 203 can include parameter inputs 204, a parameter analysis circuit 205, a storage device 214, and a notification circuit 215. Parameter inputs 204 can include a physiological marker input 206 and an other parameter input 207. Physiological marker input 206 can receive one or more physiological marker parameters generated by signal processing circuit 202, such as one or more parameters each indicative or being a measure of one or more physiological markers listed above (i-xix) or in Table 1. Other parameter input 107 can receive one or more other parameters that can be used in the determination of the state of the respiratory distress, including information entered by the patient and/or the user. In this document, a "user" can include a physician, other medical professional, or caregiver who attends the patient including monitoring and/or treating the patient using the present system. In some example, the "user" can also include the patient, such as when the patient is allowed to adjust certain operations of the system.

Parameter analysis circuit 205 can represent an example of parameter analysis circuit 105 and can determine the state of the respiratory distress based on the patient condition parameters received by parameter inputs 204. In one embodiment, parameter analysis circuit 205 determines a patient condition metric being a linear or nonlinear combination of the patient condition parameters, and produces one or more respiratory distress indicators indicating the state of the respiratory distress based on the patient condition metric. The patient condition parameters includes at least the one or more physiological marker parameters. Storage device 214 can store the state of the respiratory distress determined by parameter analysis circuit 205 over time. In various embodiments, parameter analysis circuit 205 can produce and analyze a trend of the state of the respiratory distress using the stored states. The trend allows respiratory distress analyzer 203 to identify changes in the patient's condition including changes in the state of the respiratory distress.

Notification circuit 215 can present the one or more respiratory distress indicators produced by parameter analysis circuit 205 to the patient and/or the user (e.g., through a user interface of a system illustrated in one of FIGS. 5-7 and discussed below). Notification circuit 215 can include a classification circuit 216 and an alert circuit 217. Classification circuit 216 can stratify a risk for exacerbation of the respiratory distress for the patient. The risk can be categorized based on individual characteristics of the patient, including, for example, diet, pollen levels, allergies, activity levels, disease history, and/or sleep quality. The risk stratification can allow respiratory distress analyzer 203 to respond to worsening signs differently for a patient currently in a low risk category versus a patient currently in a high risk category for the exacerbation, for example, in determine whether and how to notify the patient and/or the user. Alert circuit 217 can produce an alert notifying a need for medical intervention based on the one or more respiratory distress indicators. In one embodiment, alert circuit 217 produces the alert based on the one or more respiratory distress indicators and the patient's risk category stratified by classification circuit 216. Depending on the stratified risk category, alert circuit 217 can produce an alert notifying a detection of the respiratory distress and a distinct alert notifying a prediction of the respiratory distress, and/or distinct alerts notifying different risk categories.

Signal processing controller 213 can receive a processing control signal and adjust the processing of the patient condition signals based on the processing control signal. The processing control signal can include a signal indicative of a physical state of the patient, such as a signal indicating an activity level of the patient (e.g., sensed from the patient using an activity sensor) or a signal indicating whether the patient is sleeping (e.g., sensed from the patient using a sleep sensor). For example, the activity or sleep sensor may trigger sampling for heart rate, respiration rate, and lung sounds and processing of these signals only when the patient is sleeping or at rest. In various embodiments, signal processing controller 213 can adjust a sampling rate of signal processing circuit 202 based on the processing control signal and/or activate or deactivate signal processing circuit 202 based on the processing control signal. In various embodiments, signal processing controller 213 can also activate or deactivate other portions of respiratory distress monitoring circuit 200 and/or other portions of the present system (e.g., monitoring devices acquiring the patient condition signals) based on the processing control signal.

Figure 3:
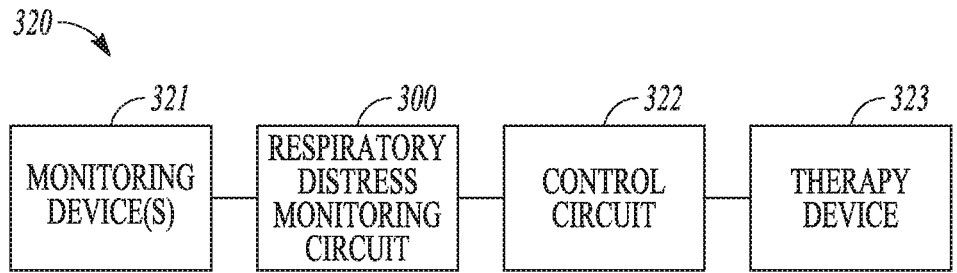
FIG. 3 illustrates an embodiment of system for monitoring and treating respiratory distress, wherein the circuit of FIG. 1 or FIG. 2 may be used.

FIG. 3 illustrates an embodiment of system 320 for monitoring and treating the respiratory distress. Respiratory distress monitoring circuit 100 or 200 can be implemented in system 320. For monitoring purposes, system 320 includes at least one or more monitoring devices 321 and a respiratory distress monitoring circuit 300. For monitoring and therapeutic purposes, system 320 can include monitoring device(s) 321, respiratory distress monitoring circuit 300, a control circuit 322, and a therapy device 323. Monitoring device(s) 321 acquire the patient condition signals. For example, monitoring device(s) 321 can include one or more sensors to sense one or more signals related to the patient's medical condition including the state of respiratory distress and produce the one or more sensor signals of the patient condition signals. Therapy device 323 can deliver one or more therapies treating the respiratory distress, including prevention of a predicted exacerbation. Control circuit 322 can control the delivery of the one or more therapies based on the state of the respiratory distress as determined by respiratory distress monitoring circuit 300. Examples of respiratory distress monitoring circuit 300 include medical condition monitoring circuits 100 and 200. In addition to, or in place of, delivering the one or more therapies, system 320 can also recommend to the patient or the user actions to take based on the patient's conditions including the state of the respiratory distress. In various embodiments, system 320 is a closed-loop therapy system, with monitoring device(s) 321 sensing effects of delivery of the one or more therapies for adjusting the delivery based on the effects.

In one embodiment, monitoring device(s) 321, respiratory distress monitoring circuit 300, control circuit 322, and therapy device 323 are integrated into a single medical device. In other embodiments, monitoring device (s) 321, respiratory distress monitoring circuit 300, control circuit 322, and therapy device 323 can be implemented as two or more medical devices communicatively coupled to each other to form system 320. These two or more devices can be any combination of implantable, wearable, handheld, and/or remote devices.

In various embodiments, system 320 can include an implantable medical device that includes an implantable drug pump and/or a neuromodulation device (e.g., for delivering vagus nerve stimulation, pulmonary vagal fiber block therapy, and/or superior laryngeal nerve block therapy) to be used as therapy device 323. In various embodiments, such as when the patient is not connected to a therapy device, system 320 can send alerts or notifications to the patient and/or the user when the condition including the state of the respiratory distress is worsening and/or when medical intervention becomes necessary or recommendable. System 320 can detect and/or predict an exacerbation of the respiratory distress based on early or late stage of worsening symptoms and slow or rapid onset. For example, system 320 can send early stage warnings to the patient only and late stage warnings to the user in addition to the patient. In another example, system 320 can notify the patient in a slow onset for the patient to take action but notify the user in addition to the patient in a rapid onset. In various embodiments, system 320 can be used in combination with a medical condition management plan for the patient to follow, for example, by notifying the patient of the state and/or risk category of the respiratory distress such that the patient can adjust medication and/or daily activities accordingly.

In various embodiments, signal inputs 101 or 201 can receive environmental information related to the state of the respiratory distress, and parameter analysis circuit 105 or 205 can determine the state of the respiratory distress based on one or more physiological marker parameters and the received environmental information. Examples of the environmental information include time of day, time of year, GPS location, pollen levels, pollution levels, humidity levels, web information on local news, hospital admissions, and/or information on disease epidemic (e.g., flu or cold). The environmental information can be sensed using one or more sensors of monitoring device(s) 321 and/or provided by external sources.

In various embodiments, signal inputs 101 or 201 can receive user-input data related to the state of the respiratory distress. The user-input data can be entered by the patient and/or the user. Parameter analysis circuit 105 or 205 can determine the state of the respiratory distress based on the one or more physiological marker parameters and one or more of the received environmental information and the user-input data. Examples of the user data include a log of the patient's actual asthma attacks and/or COPD exacerbations, pharmaceutical use information, and/or allergies. In various embodiments, notification circuit 215 can provide the patient with custom recommendations based upon the user-input data.

In various embodiments, circuits of system 320, including its various embodiments discussed in this document, may be implemented using a combination of hardware and software. For example, the circuits may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
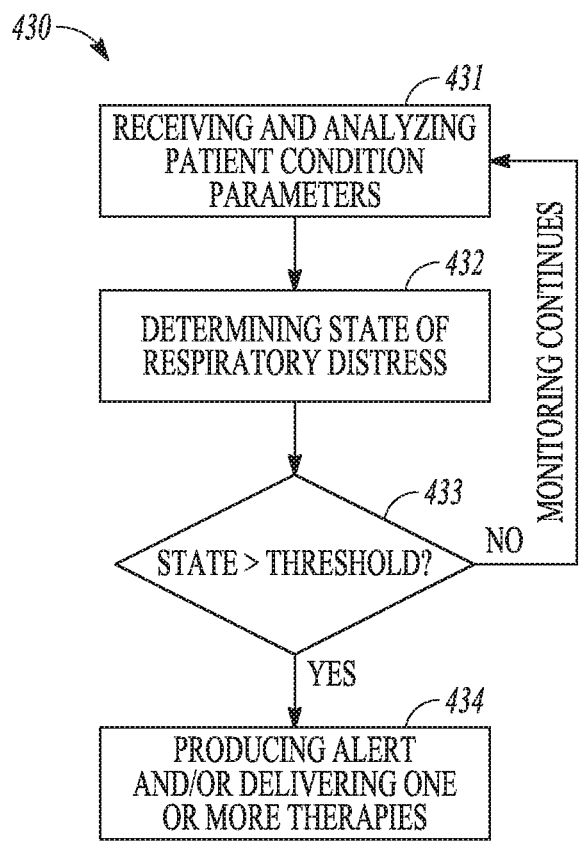
FIG. 4 illustrates an embodiment of a method for monitoring and treating respiratory distress, such as may be performed by the system of FIG. 3.

FIG. 4 illustrates an embodiment of a method 430 for monitoring and treating respiratory distress. In one embodiment, method 430 can be performed using system 320.

At 431, patient condition parameters are received and analyzed. The patient condition parameters can include one or more physiological marker parameters each indicative or being a measure of one or more physiological markers of the respiratory distress, such as those listed above (i-xix) or in Table 1. In some embodiments, the patient condition parameters can also include other parameters useable in determining the state of the respiratory distress, such as inputs from the patient and/or the user.

At 432, the state of the respiratory distress is determined based on an outcome of the analysis of the patient condition parameters. In one embodiment, a patient condition matrix is produced as a liner or nonlinear function of the patient condition parameters, and one or more indicators of the state of the respiratory distress are produced based on the patient condition metric.

If the state of the respiratory distress (e.g., a quantitative measure of the state) does not exceed a threshold at 433, method 430 continues from 431 again. If the state of the respiratory distress exceeds the threshold at 433, an alert is produced to notify the patient and/or the user, and/or one or more therapies treating the respiratory distress are delivered, at 434. Method 430 can continue from 431 again to monitor the state of the respiratory distress including the effect of the delivery of the one or more therapies and/or other medical intervention resulting from the alert.

Figure 5:
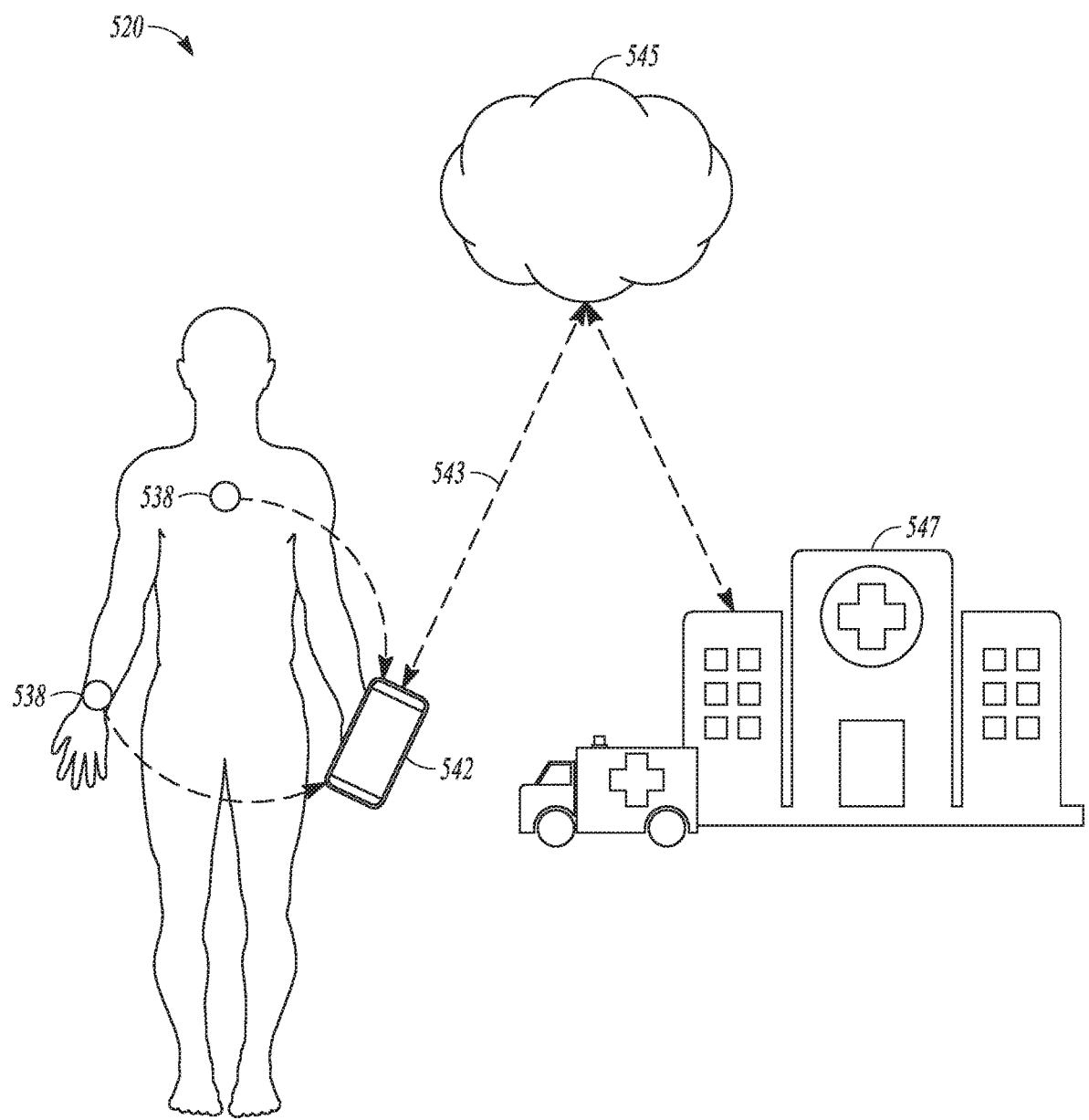
FIG. 5 illustrates an embodiment of a system for monitoring respiratory distress.

FIG. 5 illustrates an embodiment of a system 520 for monitoring respiratory distress. System 520 can represent an example of system 320 (with monitoring functions only). As illustrated in FIG. 5, system 520 can include monitoring devices 538, a portable device 542, a network 545 communicatively coupled to portable device 542 via a wired or wireless communication link 543, and a medical facility 547 communicatively coupled to network 545. Respiratory distress monitoring circuit 300 can be distributed in portable device 542 and/or network 545. In various embodiments, portable device 542 can be implemented as a dedicated device or in a generic device such as a smartphone, a laptop computer, or a tablet computer. Monitoring devices 538 can include monitoring devices 321 each being an implantable or non-implantable sensor communicatively coupled to portable device 542 via a wired or wireless link. Information such as the patient condition signals, the patient condition parameters, and/or the one or more respiratory distress indicators can be received and/or produced by portable device 542 and transmitted to network 545 via communication link 543 to be stored, further analyzed, and/or inform the user. When the patient's medical condition including the state of the respiratory distress (e.g., as determined in portable device 542 or network 545) indicates that the patient needs medical attention, a notification will be transmitted to medical facility 547 from network 545.

Figure 6:
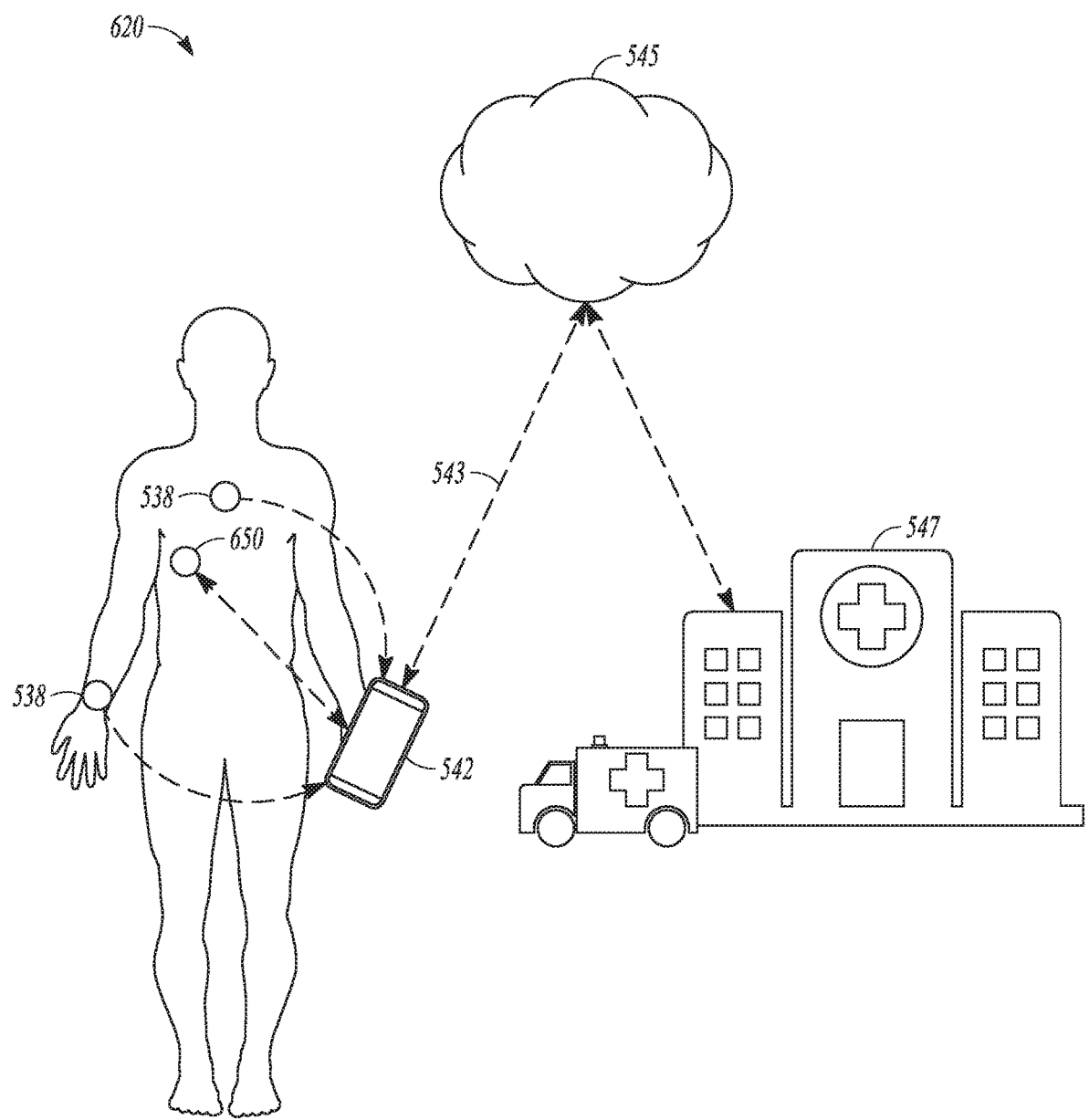
FIG. 6 illustrates an embodiment of a system for closed-loop therapy delivery for treating respiratory distress.

FIG. 6 illustrates an embodiment of a system 620 for closed-loop therapy delivery for treating respiratory distress. System 620 can represent another example of system 320. As illustrated in FIG. 6, system 620 includes the components of system 520 and a therapy device 650. Therapy device 650 can be an example of therapy device 323 and can be an implantable or non-implantable device communicatively coupled to portable device via a wired or wireless communication link. Control circuit 322 can be implemented in portable device 542 and/or therapy device 323. In various embodiments, system 320 is implemented in system 620 as a closed-loop system for monitoring and treating at least the respiratory distress.

Example: Non-Invasive System

System 320 can be implemented as a non-invasive, minimally invasive, partially implantable, or fully implantable system. When system 320 is a non-invasive system, one or more monitoring devices 321 include one or more non-invasive monitoring devices. In various embodiments, the one or more non-invasive monitoring devices can include one or more passive monitors, one or more wearable devices, one or more mobile cellular devices, one or more adhesive patches, and/or one or more any other forms of non-invasive monitoring devices suitable for acquiring the needed patient condition signals.

A passive monitor (also known as in-home patient monitor, bedside monitor, remote patient monitor, passive patient monitor, passive in-home monitor, passive bedside monitor, etc.) can identify the patient and sense one or more signals from the identified patient. In various embodiments, a passive monitor can use radio or microwave signals or cameras (visible or infrared) to identify individuals and detect signals. Radio or microwave signals can be used in this manner due to differences in wave reflection time back to the emitter, allowing for respiratory rate, heart rate, and movement to be detected. Cameras can be used based on minute color changes in the skin which occurs due to blood flow. Examples of physiological markers of the respiratory distress that can be sensed using a passive monitor include respiration rate, heart rate and HRV (including frequency and time domain measures), RSA (using respiratory and cardiac signals to derive RSA metrics from the expiratory and inspiratory periods of physiological signals, for example, acquired using two different filters to derive a respiratory rate signal and a heart rate signal, or using two passive monitors), activity, movement to capture activity levels and sleep quality metrics (sleep disturbances will appear as high-amplitude spikes in the data stream), and/or blood pressure (e.g., as indicated by pulse transit time measure captured by a bedside camera). A passive monitor can include a microphone to detect respiratory or lung sounds, coughing, and/or vocal expression. A passive monitor can include an ultrasound transmitter and receiver to detect patient movement and/or patient respiration.

A wearable monitor (also known as wearable, healthcare wearable, wearable sensor, etc.) can be worn by the patient and sense one or more signals from the patient. Examples of wearable monitors can include wrist-worns, rings, necklaces, anklets, and sensors embedded in clothing (chest patch for example). Examples of physiological markers of the respiratory distress that can be sensed using a wearable monitor include respiration rate (e.g., measured with accelerometers, gyroscopes, photoplethysmography (PPG) sensors, and/or impedance sensors), heart rate and heart rate variability (including frequency and time domain measures, e.g., measured via biopotential, bioimpedance, and/or PPG sensors), galvanic skin response (including time and frequency domain measures), blood pressure (including measurements such as systolic and diastolic blood pressure, pulse transit time, wave amplitude, and/or volume, BRS (captured by blood pressure and heart rate signals paired with one or more of activity, posture, and/or respiration signal), chemical marker (e.g. measured by sweat analysis), activity levels, sleep quality, vocal expression analysis, lung sounds, coughing, wheezing, and or external factors including location tracking, ambient temperature, and/or ambient humidity.

A mobile cellular device can be worn or carried by the patient or placed near the patient and sense one or more signals from the patient. An example of the mobile cellular device includes a smartphone with a patient monitoring application installed. Mobile cellular devices that allow for intermittent sensing of the patient condition signals include, for example: microphone for vocal expression analysis, accelerometer for activity tracking, global positioning system (GPS) for location tracking and associated external factors including temperature, ambient humidity, and/or allergen levels, and/or sensors coupled to mobile devices such as ECG sensors for recording heart rate, HRV (time and frequency domain measures), respiration rate, and RSA. Mobile cellular devices can also be used for continuous sensing of the patient condition signals while the patient is sleeping if the mobile devices are placed on mattress while sleeping. Examples of the patient condition parameters generated from signals continuously sensed include heart rate and HRV (time and frequency domain measures), respiration rate, RSA, and sleep quality parameters.

An adhesive patch including one or more sensors can be attached to the patient and sense one or more signals from the patient. Examples of physiological markers of the respiratory distress that can be sensed using an adhesive patch include ECG, heart sounds, HRV, respiration rate, RSA, lung sounds, and/or electromyogram (EMG) for neural respiratory drive. An adhesive patch can also be made capable of communicating with the user and/or insurance company to indicate when it is being worn by the patient to ensure compliance of treatment instructions and/or requirements.

Figure 7:
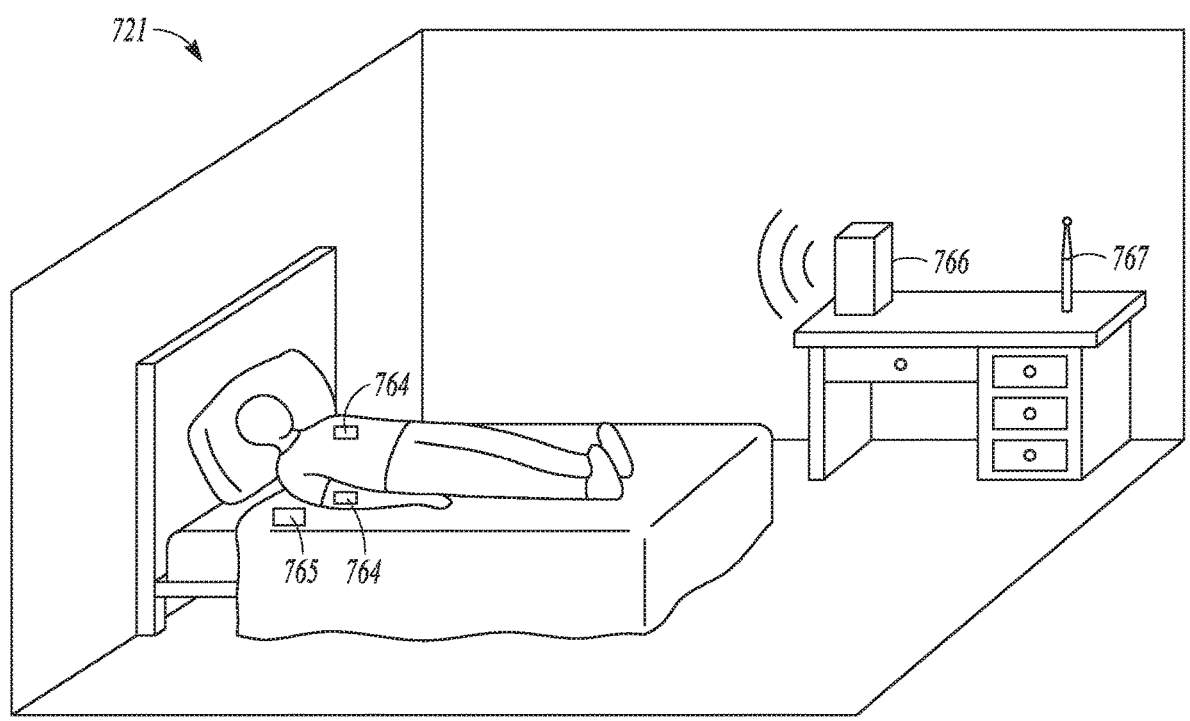
FIG. 7 illustrates an embodiment of a system of non-invasive monitoring devices for monitoring respiratory distress.

FIG. 7 illustrates an embodiment of a system of non-invasive monitoring devices 721 for monitoring respiratory distress. Monitoring devices 721 can be an example of monitoring devices 321 and an example of using non-invasive (non-implantable) sensors for monitoring devices 538 in system 520 or 620. For the purpose of illustration, but not restriction, FIG. 7 shows non-invasive monitoring devices 764, 765, 766, and 767. Monitoring device 764 can be wearable devices including sensors for sensing, for example, blood volume pulse, temperature, bodily sounds, chemical markers, and/or activity level. Monitoring device 765 can be a passive bed monitor including one or more sensors for sensing, for example, sleep quality, hate rate, respiratory rate, and/or HRV. Monitoring device 766 can be a passive in-home monitor including one or more radiowave sensors, ultrasound sensors, and/or cameras for sensing, for example, sleep quality, heart rate, and/or respiratory rate. Monitoring device 767 can be a bodily fluid sensor such as a saliva sensor for inflammatory markers (e.g., incorporated into a toothbrush for daily use).

In various embodiments, monitoring device(s) 321 can include one or more minimally invasive monitoring devices. For example, monitoring device(s) 321 can include sensors integrated with minimally invasive or borderline invasive devices such as diabetes monitor, microneedles, contact lens, tattoo, inhalable sensors, ingestible sensors, artificial limbs, and/or sensor placed in the nostril or sinus. In various embodiments, monitoring device(s) 321 can include one or more monitoring devices each integrated with one or more therapy devices such as nebulizer, respirator, continuous positive airway pressure (CPAP) machine, and/or chest compression devices. In various embodiments, non-invasive and/or minimally invasive monitoring devices, when used individually or in combination, can provide a system for the patients to track symptoms objectively over time, to identify when the patient's condition is deteriorating, and to provide information to the patient and/or the user when appropriate. These monitoring devices can also provide inputs to a closed-loop therapy system.

Example: Monitoring Respiration-Mediated Parameter

Figure 8:
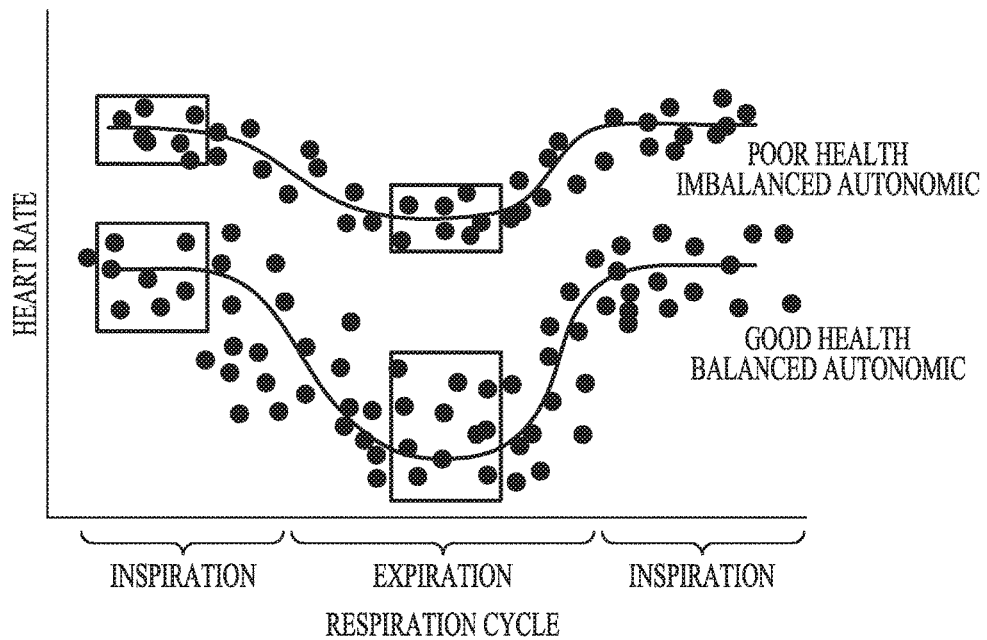
FIG. 8 illustrates an example of short-term heart rate variability (HRV) throughout a respiration cycle under healthy and diseased conditions.
Figure 9:
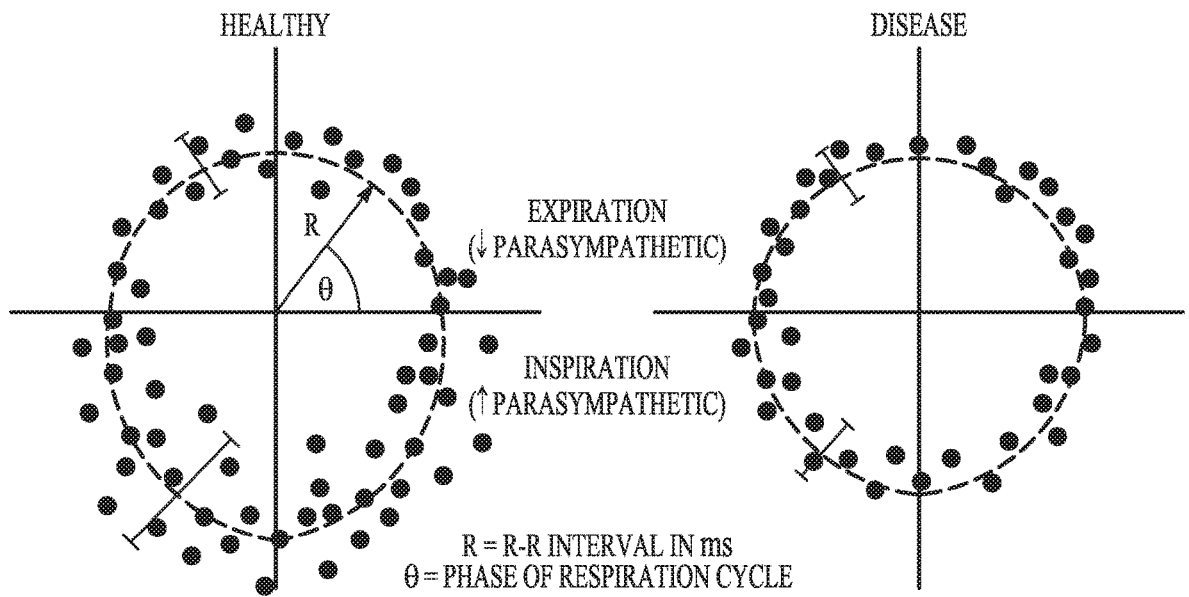
FIG. 9 illustrates another example of short-term HRV throughout a respiration cycle under healthy and diseased conditions.

In various embodiments, the state of the respiratory distress can be monitored using one or more respiration-mediated physiological parameters, such as one or more measures of respiratory sinus arrhythmia (RSA), that are indicative of the patient's autonomic balance. The state of the respiratory distress can be measured by a degree of autonomic imbalance. FIG. 8 illustrates an example of short-term heart rate variability (HRV) throughout a respiration cycle under healthy and diseased conditions. FIG. 9 illustrates another example of short-term HRV throughout a respiration cycle under healthy and diseased conditions. RSA is characterized by the magnitude of HRV at different time points along the respiration cycle and/or ratios between HRV at various time points along the respiration cycle. In various embodiments, the one or more patient condition parameters and/or metrics can include one or more measures of the RSA for determine the state of the respiratory distress, such as asthma or COPD.

Respiratory distress monitoring circuit 100, 200, or 300 can be configured to monitor the state of the respiratory distress using one or more respiration-mediated physiological parameters, such as one or more measures of RSA. Referring back to FIG. 1, Signal inputs 101 can receive one or more respiratory signals and one or more cardiac signals. The one or more respiratory signals are indicative of respiratory cycles including inspiratory and expiratory phases. The one or more cardiac signals are indicative of cardiac cycles including at least ventricular depolarizations (R-waves). Signal processing circuit 102 can be configured to process the one or more respiratory signals and the one or more cardiac signals and to generate one or more respiration-mediated physiological parameters indicative of the state of the respiratory distress, such as one or more RSA parameters being one or more measures of the RSA. Respiratory distress analyzer 103 can be configured to determine the state of the respiratory distress using the one or more respiration-mediated physiological parameters. Physiological marker input 106 can receive the one or more respiration-mediated physiological parameters. Parameter analysis circuit 105 can be configured to analyze the one or more respiration-mediated physiological parameters received from signal processing circuit 102 and determine the state of the respiratory distress using an outcome of the analysis.

Referring back to FIG. 2, signal inputs 201 can be configured to include a respiratory signal input to receive the one or more respiratory signals and a cardiac signal input to receive the one or more cardiac signals. Signal processing circuit 202 can be to process the one or more respiratory signals and the one or more cardiac signals and to generate the patient condition parameters indicative of the state of the respiratory distress. The patient condition parameters include the one or more respiration-mediated physiological parameters indicative of the state of the respiratory distress, such as one or more RSA parameters each being a measure of the RSA. Respiratory distress analyzer 203 can be configured to determine the state of the respiratory distress based on the one or more respiration-mediated physiological parameters. Physiological parameter input 206 can be configured to receive the one or more respiration-mediated physiological parameters. The one or more respiration-mediated physiological parameters can include, but are not limited to, one or more of the following parameters:
  (a) Absolute heart rate, HRV, or R-R interval during inspiration and expiration;
  (b) Change in heart rate, HRV, or R-R interval over respiration cycle;
  (c) Ratio of heart rate, HRV or R-R interval during expiration to inspiration;
  (d) Each in (a)-(c) above averaged over time (e.g., an ensemble average over multiple respiratory cycles);
  (e) Measure of deviation from normal respiration heart rate cycling (e.g., heart rate or R-R interval plotted as a function of respiration phase);
  (f) Frequency-domain parameters of heart rate and HRV as functions of respiration; and/or
  (g) Phase of the respiratory signal and corresponding cardiac signal.

Parameter analysis circuit 205 can be configured to determine the state of the respiratory distress based on at least the one or more respiration-mediated physiological parameters. In one embodiment, parameter analysis circuit 205 can be configured to produce a respiration-mediated signal metric including a linear or nonlinear combination of the respiration-mediated physiological parameters and to produce the one or more respiratory distress indicators indicating the state of the respiratory distress based on the respiration-mediated signal metric. In various embodiments, respiratory distress monitoring circuit 300 can be configured to monitor the state of the respiratory distress using the one or more respiration-mediated physiological parameters in combination with any one or more other physiological marker parameters, and/or other parameters related to the respiratory disorder, that are discussed in this document.

Referring back to FIG. 3, when respiratory distress monitoring circuit 300 is configured to monitor the state of the respiratory distress using the one or more respiration-mediated physiological parameters, such as the one or more measures of RSA, monitoring device(s) 321 can include one or more sensors that can be configured to sense the one or more respiratory signals and the one or more cardiac signals. In various embodiments, monitoring device(s) 321 can include an implantable, injectable, non-invasive, wearable, or passive monitoring device, or a combination of any of these devices, including one or more sensors to acquire, for example, a signal corresponding to respiration to indicate period of inspiration and expiration and a signal corresponding to heart rate to evaluate changes in R-R intervals during periods of the respiratory cycle identified by the respiration signal. These signals allow parameter analysis circuit 205 to produce a metric of respiration-mediated physiological signal. In various embodiments, the one or more respiration signals can be acquired directly or indirectly using, for example, one or more of the following:
  (a) Respiration sensor (e.g., patient-contacting sensor such as chest and abdominal movement sensor, acoustic sensor, airflow sensor, muscle strain sensor, and/or impedance sensor, and/or non-contacting sensor such as radio or microwave based tissue movement sensor, optical sensor, acoustic sensor, camera, and/or accelerometer or gyroscope);
  (b) ECG sensor (for deriving periods of inspiration and expiration from ECG, which is modulated by respiratory activity);
  (c) Heart sound sensor (for deriving periods of inspiration and expiration from a heart sound signal that is modulated by respiratory activity); and/or
  (d) Blood pressure sensor (e.g., PPG sensor, blood pressure cuff, and/or invasive blood pressure sensor).

The one or more cardiac signals (or surrogate respiration-mediated signals) can be acquired using, for example, one or more of the following:
  (a) ECG sensor (ECG is modulated by respiratory activity);
  (b) Heart sound sensor (acoustic vibrations from the cardiac cycle are modulated by respiratory activity);
  (c) Blood pressure or flow sensor (e.g., PPG sensor, blood pressure cuff, and/or invasive blood pressure sensor);
  (d) Blood gas concentration sensor (e.g., pulse oximeter and/or invasive blood gas sensor; and/or
  (e) Nerve sensor for direct neural recordings (e.g., surface electrodes and/or invasive nerve recording sensors).

In various embodiments, monitoring device(s) 321 can include one or more sensors in one or more remote devices coupled to respiratory distress monitoring circuit 300 via one or more wireless or wired communication links. Such one or more remote devices can include, but are not limited to, one or more of the following:
  (a) Invasive or noninvasive device for processing sensor input data;

(b) Personal device for alerts and notification on pain levels; and/or (c) Invasive or noninvasive devices used as part of a closed-loop system, including a closed-loop systems where the patient closes the loop by himself/herself.

Figure 10:
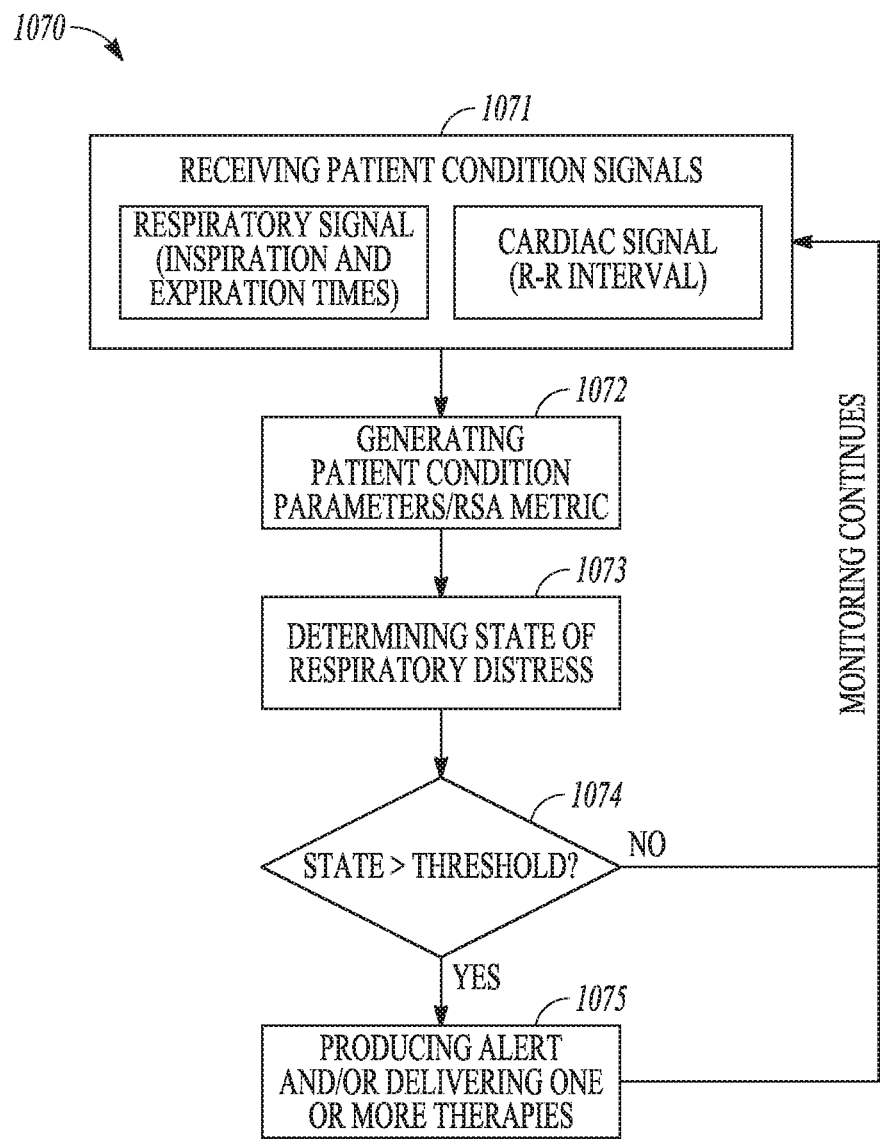
FIG. 10 illustrates an embodiment of a method for monitoring respiratory distress based on an RSA metric.

FIG. 10 illustrates an embodiment of a method 1070 for monitoring respiratory distress based on a patient condition metric derived from respiratory and cardiac signals, such as an RSA metric. Method 1070 can be performed using system 320, which can be implemented in system 520 or 620.

At 1071, patient condition signals are received. The patient condition signals include a respiratory signal indicative of inspiration and expiration times and a cardiac signal indicative of R-R interval (i.e., as referred to as cardiac cycle length or ventricular rate interval, measure as the time interval between consecutive R-waves). At 1072, the patient condition metric (e.g., the RSA metric) is determined using the respiratory and cardiac signals. At 1073, the state of the respiratory distress is determined based the patient condition metric such as the RSA metric. If the state of the respiratory distress (e.g., a quantitative measure of the state) does not exceed a threshold at 1074, method 1070 continues from 1071 again. If the state of the respiratory distress exceeds the threshold at 1074, an alert is produced to notify the patient and/or the user, and/or one or more therapies treating the respiratory distress are delivered, at 1075. Method 1070 can continue from 1071 again to monitor the state of the respiratory distress including the effect of the delivery of the one or more therapies and/or other medical intervention resulting from the alert.

Figure 11:
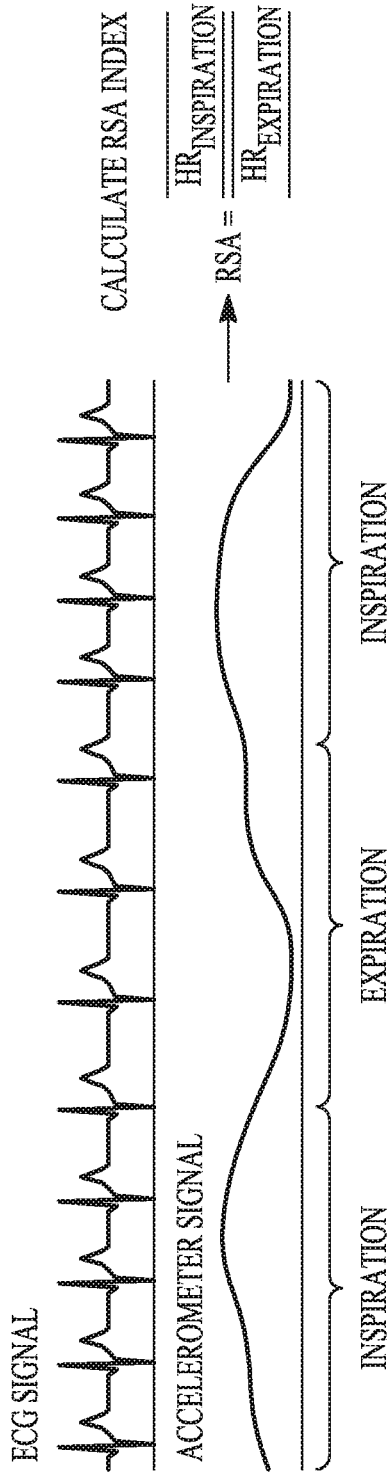
FIG. 11 illustrates an example of a method for monitoring RSA using electrocardiographic (ECG) and accelerometer signals.
Figure 12:
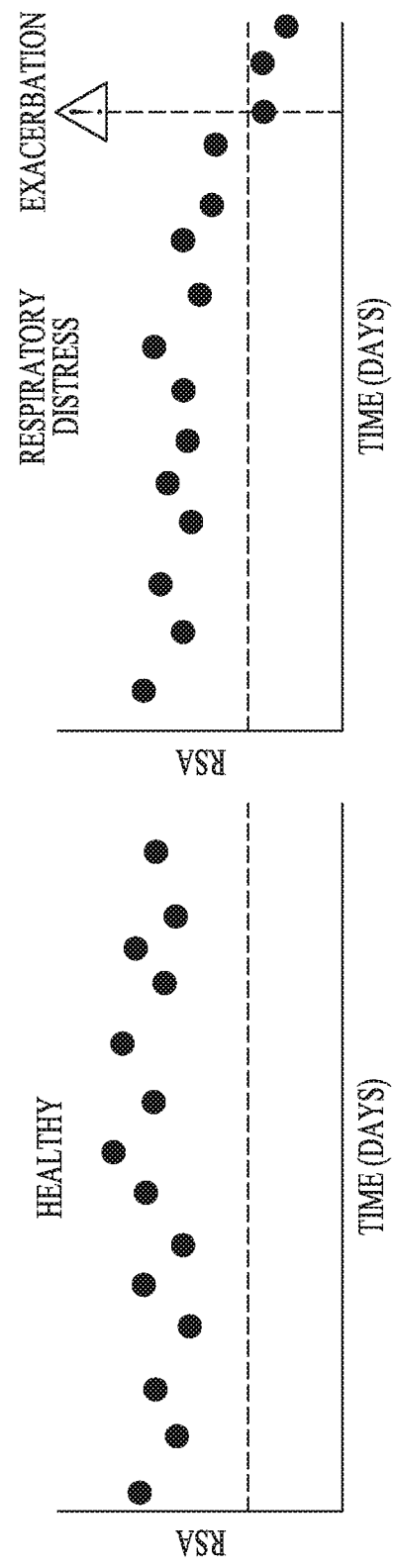
FIG. 12 illustrates an example of RSA information acquired using the method of FIG. 11 and allowing for predicting or detecting exacerbation of respiratory distress.

FIG. 11 illustrates an embodiment of a method for monitoring RSA using ECG and accelerometer signals. In one embodiment, the ECG and accelerometer signals are sensed using a chest patch attached to the chest of the patient. In another embodiment, the ECG and accelerometer signals are sensed using an implantable cardiac monitor (ICM) that is placed within the patient. Mean heart rates are calculated using R-waves detected from the ECG signal separately for inspiration and expiration periods detected from the accelerometer signal. An RSA index (representing an autonomic measure) is calculated as a ratio of the mean heart rate during inspiration to the mean heart rate during expiration. FIG. 12 illustrates an example of RSA index plotted against time for healthy and diseased (with the respiratory distress. An exacerbation of the respiratory distress is detected or predicted when the RSA index falls below a threshold (dash line). In various embodiments, different thresholds can be used for detection and prediction. An alert can be produced to notify the patient and/or the user that exacerbation of the respiratory distress is detected. A distinct alert can be produced to notify the patient and/or the user that exacerbation of the respiratory distress is predicted.

Example: Monitoring Brs

Figure 13:
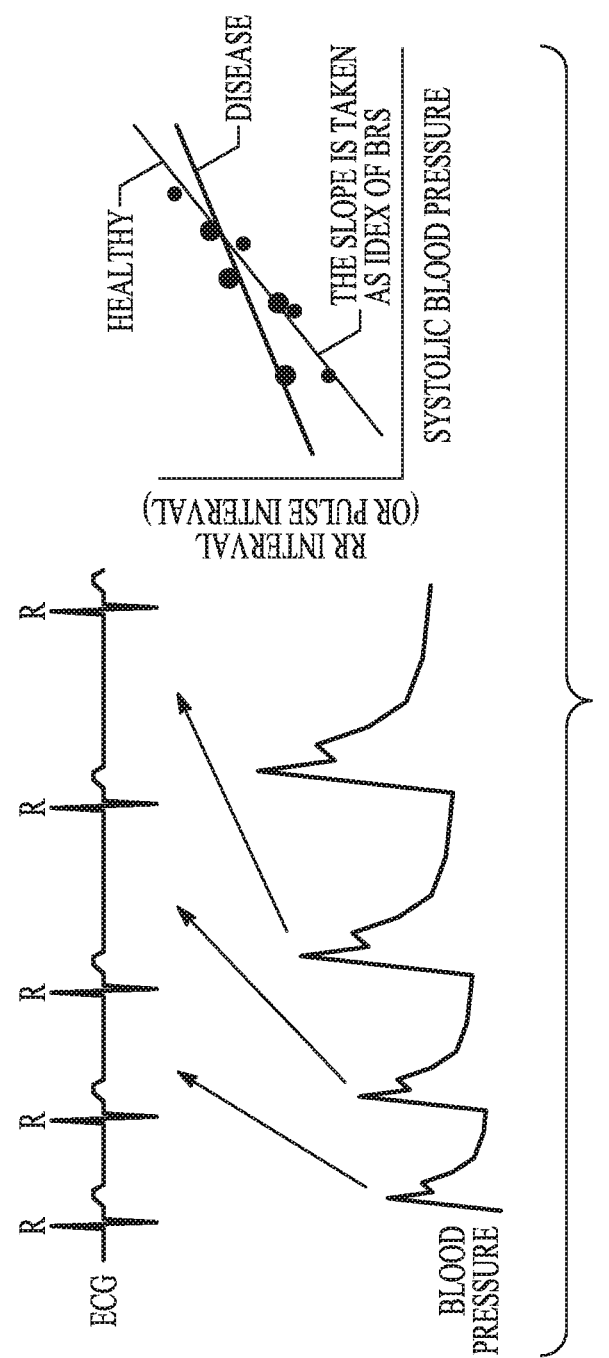
FIG. 13 illustrates an example of BRS under healthy and diseased conditions.

In various embodiments, the state of the respiratory distress can be monitored using one or more respiration-mediated physiological parameters, such as one or more measures of baroreflex sensitivity (BRS) that are indicative of the patient's autonomic balance. The state of the respiratory distress can be measured by a degree of autonomic imbalance. FIG. 13 illustrates an example of BRS under healthy and diseased conditions. With abnormal autonomic activity associated with the respiratory distress, the change in heart rate in response to change in blood pressure is attenuated, resulting in decreased BRS. This attenuation in BRS can lead to impaired sympathetic inhibition, elevated blood pressure, and worsening of the respiratory distress. In various embodiments, the one or more patient condition parameters and/or metrics can include one or more measures of the BRS for determine the state of the respiratory distress, such as asthma or COPD.

Respiratory distress monitoring circuit 100, 200, or 300 can be configured to monitor the state of the respiratory distress using one or more BRS parameters being one or more measures of BRS. Referring back to FIG. 1, Signal inputs 101 can receive one or more blood pressure signals, one or more cardiac signals, and one or more physical state signals. The one or more respiratory signals are indicative of respiratory cycles including inspiratory and expiratory phases. The one or more cardiac signals are indicative of cardiac cycles including at least ventricular depolarizations (R-waves). The one or more physical state signals each indicate a physical state or change in the physical state of the patent that affects the patient's BRS. Signal processing circuit 102 can be configured to process the one or more blood pressure signals, the one or more cardiac signals, and the one or more physical state signals and to generate the one or more BRS parameters. Respiratory distress analyzer 103 can be configured to determine the state of the respiratory distress using the one or more BRS parameters. Physiological marker input 106 can receive the one or more BRS parameters. Parameter analysis circuit 105 can be configured to analyze the one or more BRS parameters received from signal processing circuit 102 and determine the state of the respiratory distress using an outcome of the analysis.

Referring back to FIG. 2, signal inputs 201 can be configured to include a blood pressure input to receive the one or more blood pressure signals, a cardiac signal input to receive the one or more cardiac signals, and a physical state input to receive the one or more physical state signals. Signal processing circuit 202 can be configured to process the one or more blood pressure signals, the one or more cardiac signals, and the one or more physical state input signals and to generate the patient condition parameters indicative of the state of the respiratory distress. The patient condition parameters include the one or more BRS parameters and one or more physical state parameters. Respiratory distress analyzer 203 can be configured to determine the state of the respiratory distress based on the one or more BRS parameters and the one or more physical state parameters. The one or more physical state parameters indicate one or more physical states of the patient that affects the patient's BRS and allow the one or more BRS parameters to be expressed as functions of the one or more physical states. Physiological parameter input 206 can be configured to receive the one or more BRS parameters and the one or more physical state parameters. The one or more BRS parameters can include, but are not limited to, one or more of the following parameters:

(a) BRS (which can vary based on minimum blood pressure and heart rate thresholds for minimum change, and can vary based on the minimum number of beats in a sequence);
(b) Range of BRS;
(c) Coherence or correlation measures;
(d) Delay or latency;
(e) Recovery times;
(f) Baroreceptor characterization—sigmoid curve and morphology;
(g) Change in cardiac measure (e.g., captured as a slope of change or as a time interval for the parameter to reach a certain percentage of the peak change);

(h) Change in blood pressure measure (e.g., captured as a slope of change or as a time interval for the parameter to reach a certain percentage of the peak change); and/or (i) Other measure(s) of baroreceptor response.

The one or more physical state parameters can include, but are not limited to, one or more of the following parameters:

(a) Respiratory cycle timing (timing of inspiration and expiration phases);

(b) Level of physical activity or exertion (e.g., indicated by the activity and respiration sensors, classified as mild, moderate, or vigorous activity)(baroreceptor response can be characterized over a continuum of levels of physical activity or exertion indicated by signals, such as activity, respiration, and/or biochemical markers, for example, by vector magnitude units (in g) over a period of time, caloric expenditure, distance traveled, or other activity or exertion measures, or a combination of these parameters);

(c) Type of posture change (e.g., indicated by the posture sensor, classified as laying to sitting, laying to standing, sitting to standing, etc.); and/or (d) Magnitude of posture change (angle) and/or time duration of posture change (seconds, or degrees/second).

The one or more BRS parameters can be stratified by values of such one or more physical state parameters.

Parameter analysis circuit 205 can be configured to determine the state of the respiratory distress based on at least the one or more BRS parameters and the one or more physical state parameters. In one embodiment, parameter analysis circuit 205 can be configured to produce a BRS metric including a linear or nonlinear combination of the one or more BRS parameters as stratified by the one or more physical state parameters and to produce the one or more respiratory distress indicators indicating the state of the respiratory distress based on the BRS metric. In various embodiments, respiratory distress monitoring circuit 300 can be configured to monitor the state of the respiratory distress using the one or more BRS parameters and the one or more physical state parameters in combination with any one or more other physiological marker parameters, and/or other parameters related to the respiratory disorder, that are discussed in this document.

Referring back to FIG. 3, when respiratory distress monitoring circuit 300 is configured to monitor the state of the respiratory distress using the one or more BRS parameters and the one or more physical state parameters, monitoring device(s) 321 can include one or more sensors that can be configured to sense the one or more blood pressure signals, the one or more cardiac signals, and the one or more physical state signals. In various embodiments, monitoring device(s) 321 can include an implantable, injectable, non-invasive, wearable, or passive monitoring device, or a combination of any of these devices, including one or more sensors to acquire, for example, one or more signals indicative of baroreceptor response and one or more signals indicative of activity level, respiration, and/or posture of the patient. In various embodiments, the one or more sensors can include, but are not limited to, one or more of the following:

(a) A sensor to directly or indirectly sense a blood pressure signal (e.g., a pressure sensor to sense the blood pressure directly through invasive or noninvasive means; a heart sound sensor to sense the second heard sound (S2), a sensor to sense pulse transit time, and/or a sensor to sense a blood volume pulse waveform;

(b) A sensor to directly or indirectly sense a cardiac signal (e.g., ECG allowing for measuring heart rate or R-R interval and/or HRV, including time and/or frequency domain measures of the HRV, and/or a heart sound signal allowing for detection of the first heart sound (S1)); and/or (c) One or more sensors to sense the physical state of the patient (e.g., activity, posture, respiration rate, and heart rate):

(i) An activity sensor including one or more of accelerometers, gyroscopes, electromyography (EMG) sensors, GPS, or other sensors indicating physical activity;

(ii) A posture sensor including one or more of accelerometers, gyroscopes, passive motion capture, or other sensors indicating postures; and/or (iii) A sensor to directly or indirectly sense the respiration rate and/or the heart rate, such as one or more of:

(1) Respiration sensor (e.g., patient-contacting sensor such as chest and abdominal movement sensor, acoustic sensor, airflow sensor, muscle strain sensor, and/or impedance sensor, and/or non-contacting sensor such as radio or microwave based tissue movement sensor, optical sensor, acoustic sensor, camera, and/or accelerometer or gyroscope);

(2) ECG sensor (for deriving periods of inspiration and expiration from ECG, which is modulated by respiratory activity);

(3) Heart sound sensor (for deriving periods of inspiration and expiration from a heart sound signal that is modulated by respiratory activity); and/or (4) Blood pressure sensor (e.g., PPG sensor, blood pressure cuff, and/or invasive blood pressure sensor).

In various embodiments, monitoring device(s) 321 can include one or more sensors in one or more remote devices coupled to respiratory distress monitoring circuit 300 via one or more wireless or wired communication links. Such one or more remote devices can include, but are not limited to, one or more of the following:

(a) Invasive or noninvasive device for processing sensor input data;

(b) Personal device for alerts and notification on pain levels; and/or (c) Invasive or noninvasive devices used as part of a closed-loop system, including a closed-loop systems where the patient closes the loop by himself/herself.

Figure 14:
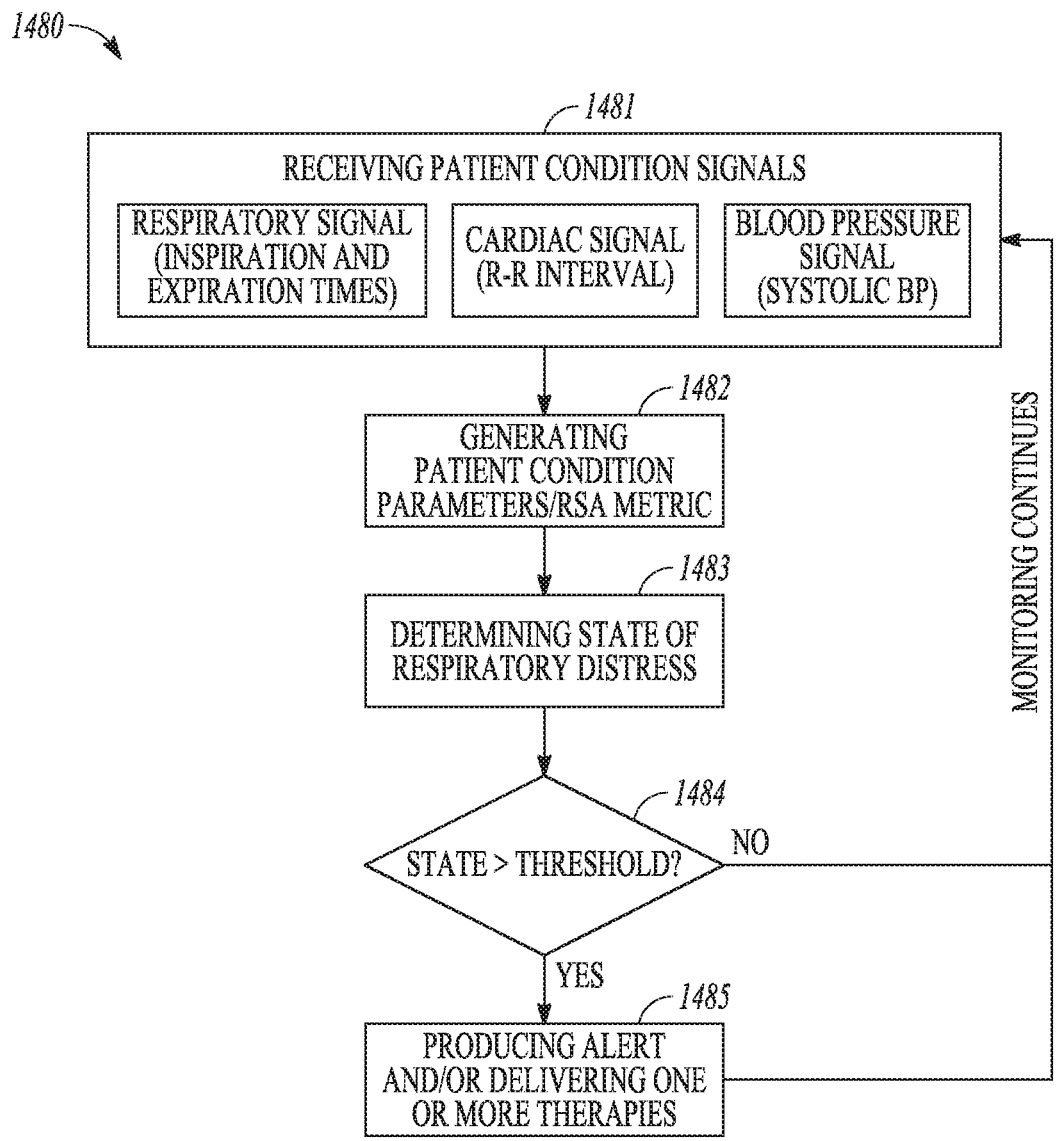
FIG. 14 illustrates an embodiment of a method for monitoring respiratory distress based on a BRS metric.

FIG. 14 illustrates an embodiment of a method 1480 for monitoring respiratory distress based on a BRS metric. Method 1480 can be performed using system 320, which can be implemented in system 520 or 620.

At 1481, patient condition signals are received. The patient condition signals include a respiratory signal indicative of inspiration and expiration times, a cardiac signal indicative of R-R interval, and a blood pressure signal indicative systolic blood pressure. At 1482, the BRS metric is determined using the respiratory, cardiac, and blood pressure signals. At 1483, the state of the respiratory distress is determined based the BRS metric. If the state of the respiratory distress (e.g., a quantitative measure of the state) does not exceed a threshold at 1484, method 1480 continues from 1481 again. If the state of the respiratory distress exceeds the threshold at 1484, an alert is produced to notify the patient and/or the user, and/or one or more therapies treating the respiratory distress are delivered, at 1485.

Method 1480 can continue from 1481 again to monitor the state of the respiratory distress including the effect of the delivery of the one or more therapies and/or other medical intervention resulting from the alert.

Figure 15:
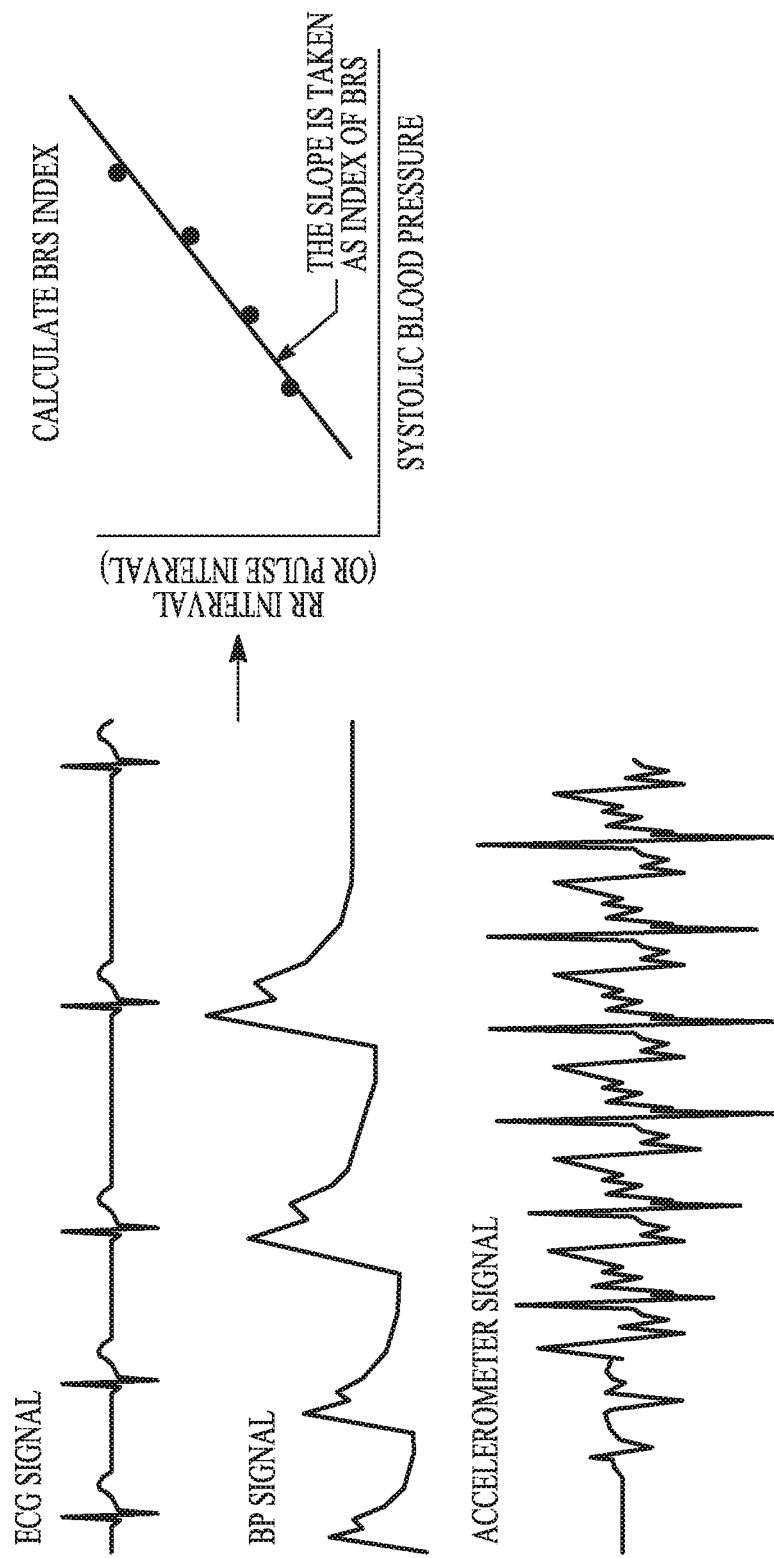
FIG. 15 illustrates an example of a method for monitoring BRS using ECG, blood pressure, and accelerometer signals.
Figure 16:
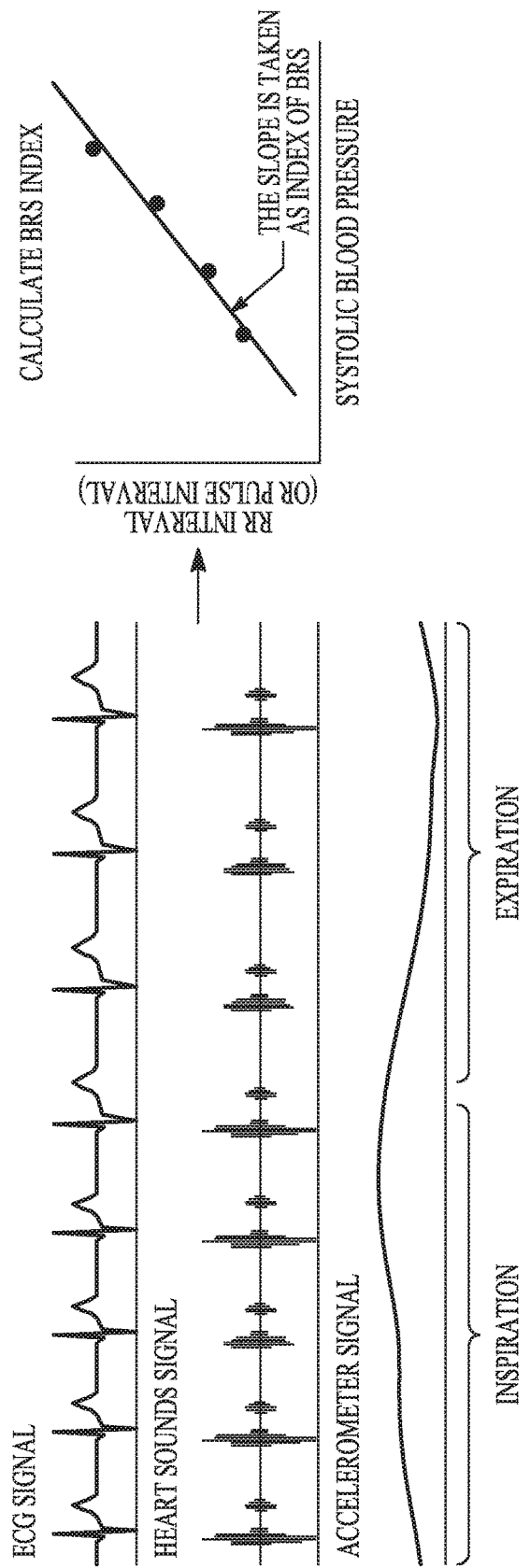
FIG. 16 illustrates an example of a method for monitoring BRS using ECG, heart sound, and accelerometer signals.
Figure 17:
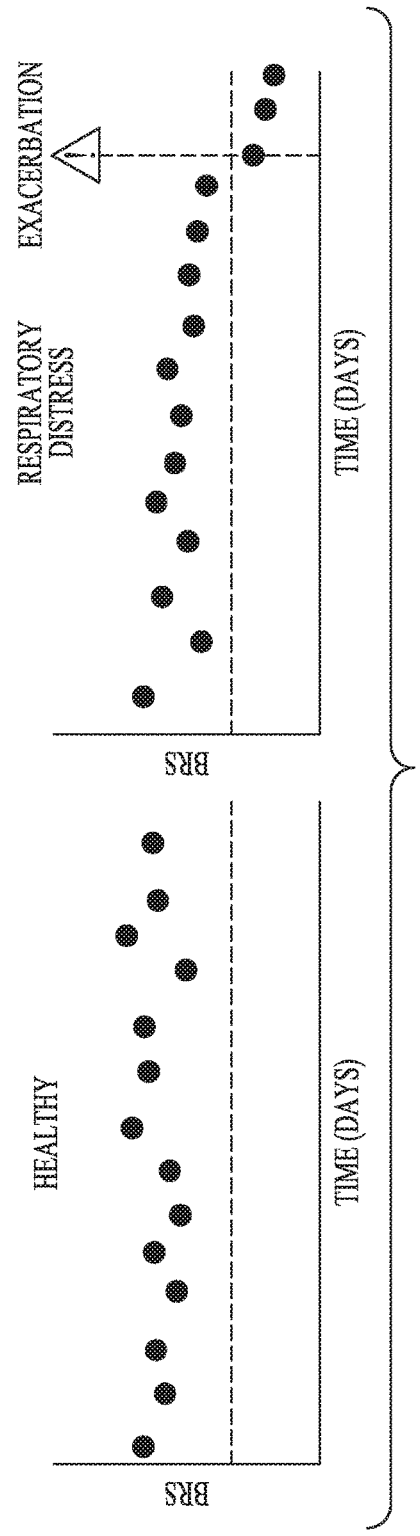
FIG. 17 illustrates an example of BRS information acquired using the method of FIG. 15 of FIG. 16 and allowing for predicting or detecting exacerbation of respiratory distress.

FIG. 15 illustrates an example of a method for monitoring BRS using ECG, blood pressure, and accelerometer signals sensed by a chest patch and a wrist-worn device on the patient. FIG. 16 illustrates an example of a method for monitoring BRS using ECG, heart sound, and accelerometer signals sensed by an ICM. The accelerometer signal is used as a respiratory signal indicative of inspiration and expiration phases uses as the patient's physical state. A BRS index (representing an autonomic measure) is calculated as a slope of a curve being the R-R interval against the systolic blood pressure (as indicated by the heart sounds). This represents one of various techniques to quantify spontaneous BRS, and allows for "up" and "down" sequences, which are controlled by different mechanisms, to be evaluated separately. Other techniques include spectral methods that look at the power of the blood pressure and heart rate signals in certain frequency ranges as well as their ratios. FIG. 17 illustrates an example of BRS index plotted against time for healthy and diseased (with the respiratory distress). An exacerbation of the respiratory distress is detected or predicted when the BRS index falls below a threshold (dash line). In various embodiments, different thresholds can be used for detection and prediction. An alert can be produced to notify the patient and/or the user that exacerbation of the respiratory distress is detected. A distinct alert can be produced to notify the patient and/or the user that exacerbation of the respiratory distress is predicted.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

TABLE 1

Physiological markers for the respiratory distress.

| Measurement | Physiology/Additional Notes | Response to Acute Exacerbation | Exemplary Method of Measurement/Devices |
|---|---|---|---|
| Respiratory Rate | Dyspnea. Increased respiratory rate and/or decreased tidal volume | Increase | Impedance measure, accelerometer, EMG, radio/micro waves, optical-based sensor, acoustic-based sensor, camera, ECG |
| Heart Rate | Increased heart rate. Overall increase in sympathetic activation and a decrease in parasympathetic activation | Increase | ECG, heart sounds, accelerometer, radio/micro waves, optical-based sensor, acoustic-based sensor, camera |
| Cough | Increased occurrence of coughing leading up to exacerbation | Increase | Microphone, accelerometer |
| Wheezing | More frequent wheezing | Increase | Microphone, accelerometer |
| Oxygen Saturation | Blood O2 saturation | Decrease | Pulse oximeter; Smartphone app |
| Central Cyanosis | Blood O2 saturation | Increase | Pulse oximeter; Smartphone app |
| Altered Consciousness | Balance and posture can be altered due to the onset (gradual or sudden) of an exacerbation | Variable | Accelerometer |
| Activity levels | Decrease in activity levels due to labored breathing | Risk factor/Trigger | Accelerometer |
| Sleep quality | Poor sleep quality, more often awakening, sleeping in an upright position | Decrease | Accelerometer, gyroscope, ECG, radio/micro waves, optical-based sensor, acoustic-based sensor, camera, GSR |
| Posture/Chest posture | Poorer posture overall, chest inflation alters chest posture | Variable | Accelerometer, gyroscope (posture) |
| Balance | Reduced balance, coordination | Decrease | Accelerometer, gyroscope (posture) |
| Gait | Altered gait pattern | Variable | Accelerometer |
| Vocal Expression | Patients with acute, severe asthma appear seriously dyspneic at rest, are unable to talk with sentences or phrases | Turbulent, altered | Microphone |
| Inflammation | Increase in inflammatory markers (blood, saliva, breath, sputum, etc.) | Increase | Chemical sensor |
| Accessory Muscle Activity | Rapid, shallow breathing changes abdominal/thoracic muscle activity | Variable | EMG |

TABLE 1-continued

Physiological markers for the respiratory distress.

| Measurement | Physiology/ Additional Notes | Response to Acute Exacerbation | Exemplary Method of Measurement/Devices |
|---|---|---|---|
| Physical Stress | Factors into patient's overall health and susceptibility to infection or other triggering event | Risk factor/ Trigger | Subjective input |
| Mental Stress | Factors into patient's overall health and susceptibility to infection or other triggering event | Risk factor/ Trigger | Subjective input |
| Menstrual Cycle | Factors into patient's overall health and susceptibility to infection or other triggering event | Risk factor/ Trigger | Subjective input |
| Time-of-day/year | Factors into patient's overall health and susceptibility to infection or other triggering event | Risk factor/ Trigger | Automatically Synced (GPS, mobile device) |
| Mucus production | Elevated mucus production blocks arieays, restricting airflow and difficulty breathing | Increase | Impedance measure |
| Airway smooth muscle contraction | Airways constrict making it difficult to breath | Increase | Impedance measure, EMG |
| Autonomic Function | | | |
| Heart Rate Variability | Decrease in heart rate variability due to the imbalance in the autonomic nervous system, with sympathetic system dominating. | Decrease | ECG, heart sounds, accelerometer, radio/micro waves, optical-based sensor. acoustic-based sensor, camera |
| Respiration Sinus Arrhythmia | Essentially the transfer function from respiration rate to R-R intervals. Another way to assess cardiac autonomic function. RSA which decreases in the presence of increased sympathetic activity/decreased parasympathetic activity. | Decrease | ECG, heart sounds, accelerometer, radio/micro waves, optical-based sensor, acoustic-based sensor, camera |
| Heart Rate Turbulence | Need premature ventricular complexes to be occurring to quantify HRT | Decrease | ECG, heart sounds |
| Baroreceptor Reflex Sensitivity | Measured after injection of phenylephrine Also a spontaneous measures that can be acquired continuously using respiration as a way to alter autonomic balance | Decrease | ECG, PPG, heart sounds |
| Heart Rate Acceleration Capacity | Sympathetic autonomic nerves act to quicken the heart and strengthen the acceleration capacity. During AECOPD, airflow obstruction aggravates autonomic function, resulting in an imbalance in the system - increase in sympathetic activity | Increase | ECG, heart sounds, accelerometer |
| Heart Rate Deceleration Capacity | Vagal nerve slows the heart rate and enhances the heart rate deceleration capacity. During AECOPD, airflow obstruction aggravates autonomic function, resulting in an imbalance in the system - decrease in parasympathetic (vagal) activity. | Decrease | ECG, heart sounds, accelerometer |

TABLE 1-continued

Physiological markers for the respiratory distress.

| Measurement | Physiology/ Additional Notes | Response to Acute Exacerbation | Exemplary Method of Measurement/Devices |
|---|---|---|---|
| Galvanic Skin Response/ Electrodermal activity | Acute stress, anxiety caused by an exacerbation results in increased sympathetic activity which causes sweat glands to fill up and skin conductance increases creating skin conductance fluctuations. | Increase | Electrodes on the hand |
| Blood Pressure | increase in blood pressure due to increased sympathetic nervous system activity and resulting vasoconstruction | Increase | PPG, S2, Pulse amplitude |
| Blood Flow | Diaphragmatic blood flow reduces during acute episodes. In the case of persistence of the severe asthma attack, ventilatory muscles cannot sustain adequate tidal volumes and respiratory failure ensues. | Decrease | PPG, S2, Pulse amplitude |
| Perfusion | Diaphragmatic perfusion reduces during acute episodes. In the case of persistence of the severe asthma attack, ventilatory muscles cannot sustain adequate tidal volumes and respiratory failure ensues. | Decrease | PPG |
| Skin Temperature | | Variable | Thermometer |
| Body Temperature | Bacterial or viral infection, may cause your body temperature to rise | Increase | Thermometer |
| Pupil Diameter | Dilation of the pupil is indicative of sympathetic activation | Increase | Camera |
| Electrooc- ulography | Correlates to autonomic tone - variable relationship depending on time/frequency domain analysis performed | Variable | Electrodes |
| Pulse Transit Time & Pulse Wave Amplitude (Alternative measure for BP) | Increased sympathetic activity constricts vasculature causing transit time and wave amplitude to decrease | Decrease | PPG |
| Normalized Pulse Volume (NPV) | Sympathetic tone causes vascular construction. NPV can be derived from finger tip PPG and also from the bottom of the ear canal. NPV is an indirect measures of autonomic tone | Decrease | PPG |
| Forced Expiratory Volume | | | |
| FEV1 | forcibly exhaled air in 1 second; mainly reflects larger airways obstruction | Decreased (decreases with stage/severity) | Thoracic impedance, accelerometers, flow sensors, ECG |
| FEV1/FVC | fixed ratio <70% defines airflow limitations. FVC = forced vital capacity | Decrease | Thoracic impedance, accelerometers, flow sensors, ECG |
| TLC | Total lung capacity is the greatest volume of gas in the lungs after maximal voluntary inspiration. Increase in TLC in COPD usually reflects lung | Increase | Thoracic impedance, accelerometers, flow sensors, ECG |

TABLE 1-continued

Physiological markers for the respiratory distress.

| Measurement | Physiology/ Additional Notes | Response to Acute Exacerbation | Exemplary Method of Measurement/Devices |
|---|---|---|---|
| | compliance due to emphysema, as thoracic compliance decreases | | |
| FRC | Functional residual capacity is the lung volume at the end of quiet expiration during tidal breathing. Increased in COPD patients. | Increase | Thoracic impedance, accelerometers, flow sensors, ECG |
| FEV3 | later fraction of forced exhalation better reflects smaller airway contributions and may be a more sensitive measure to diagnose early airway obstruction in COPD | Decrease | Thoracic impedance, accelerometers, flow sensors, ECG |
| FEV3/FEV6 | ratio of later fraction measures of forced exhalation to represent the small airways. Ratio less than the lower limit of normal as the sole abnormality identifies a distinct population with evidence of small airways disease advantage of spirometric ratios is that they have less variability than do timed forced expirations | Decrease | Thoracic impedance, accelerometers, flow sensors, ECG |
| Lung hyperinflation: TLC, FRC, RV | Absolute lung volume is evaluated by measuring the increase in total lung capacity (TLC), functional residual capacity (FRC), residual volume (RV), and decrease in inspiratory capacity (IC). Lung hyperinflation exists when TLC, FRC, and RV >= 120-130% of the predicted volume | TLC, FRC, &RV all >= 120-130% | Thoracic impedance, accelerometers, flow sensors, ECG |
| Tidal Volume (VT) | increase in displaced air between inspiration and expiration. Short rapid breathing | Increase | Thoracic impedance, accelerometers, flow sensors, ECG |
| Peak expiratory flow (PEF) | Maximum speed of expiration decreases as the airways become blocked/constricted | Decrease | Thoracic impedance, accelerometers, flow sensors, ECG |
| Forced expiratory volume (FEV) | Amount of air that can be exhaled decreases. Expiration becomes slower and more difficult | Decrease | Thoracic impedance, accelerometers, flow sensors, ECG |
| Inspiration/ expiration ratio (IER) | Normal is 1:2 at rest, 1:1 during exercise. Ratio decrease with an increasing expiration period due to difficulty breathing, expelling air from the lungs | Decrease | Thoracic impedance, accelerometers, flow sensors, ECG |
| Minute volume (MV) | Total volume of gas inhaled or exhaled in 1 minute. Rapid breathing during exacerbation | Increase | Thoracic impedance, accelerometers, flow sensors, ECG |
| Forced vital capacity (FVC) | Amount of air (total amount of air) exhaled during the FEV test. | Decrease | Thoracic impedance, accelerometers, flow sensors, ECG |
| End Expiratory volume (EEV)/ ΔrEEV | Corresponds to FRC in the presence of positive end expiration pressure. ΔrEEV is used if short term filtering is used. | Increase | Thoracic impedance, accelerometers, flow sensors, ECG |

TABLE 1-continued

Physiological markers for the respiratory distress.

| Measurement | Physiology/ Additional Notes | Response to Acute Exacerbation | Exemplary Method of Measurement/Devices |
|---|---|---|---|
| HII (hyperinflation index) | Hyperinflation causes the patient to operate on the relatively flat portion of the chest wall-lung compliance curve leading to a rapid shallow breathing pattern | Increase | Thoracic impedance, accelerometers, flow sensors, ECG |
| Airway Resistance | | | |
| Impulse Oscillometry (IOS) | Pressure oscillations are applied at the mouth to measure pulmonary resistance and reactance. Noninvasive, rapid technique requiring only passive cooperation by the patient. | Variable | Impulse oscillometry system (IOS) |
| Neural Measures | | | |
| Neural Respiratory Drive Index (NRDI) | Calculated as the product of the second intercostal space parasternal electromyography activity normalized to the peak EMG activity during a maximum inspiratory sniff manoeuver. Parasternal EMG (EMGpara) signals recorded from surface electrodes have a direct relationship with respiratory muscle load and have been shown to respond to acute change. Differentiates between "improvers" and "deteriorators" in the hospital, and was also a predictor of hospital readmittance. | Increase | EMG device |
| Diaphragmatic Changes due to Hyperinflation * Not currently measured but secondary effects due to hyperinflation could be captured | Known mechanisms of compromised diaphragmatic function secondary to hyperinflation: worsening of the length-tension relationship decrease in the zone of apposition decrease in the curvature change in the mechanical arrangement of costal and crural components increase in the elastic recoil of the thoracic cage | Variable | |
| Exhaled Breath | | | |
| Exhaled Breath Temperature | Exhaled breath temperature can be an indication of airway inflammation. Peak exhaled breath in patients with exacerbations increased and dropped down with recovery. Patients with stable COPD had decreased peak EBT in comparison to controls (non smokers and smokers) | Increase --> AECOPD Decrease --> stable COPD | eNose, SpiroNose (breathcloud.org), chemical sensor |
| Fractional exhaled nitric oxide (FeNO) | During inflammation, larger amount of NO are produced for prolonged periods. NO concentrations are known to be higher in | Increase | eNose, chemical sensor |

TABLE 1-continued

Physiological markers for the respiratory distress.

| Measurement | Physiology/ Additional Notes | Response to Acute Exacerbation | Exemplary Method of Measurement/Devices |
|---|---|---|---|
| pH - expired breath | disease such as asthma and COPD. Acidification (decrease in pH) could be a maker of airway inflammation and disease severity. pH is reduced during acute exacerbations | Decrease | eNose, chemical sensor |
| O2 - expired breath | Rapid shallow breathing, increases respiratory O2 concentrations. Reduces CO2 concentrations | Increase | eNose, chemical sensor |
| CO2 - expired breath | In early stages of acute exacerbations, patients have respiratory alkalosis | Decrease | eNose, chemical sensor |
| Volatile Organic Compounds (VOCs) | Electronic noses that can pick up VOCs to assess profile and classify patients Inflammatory related and detectable in exhaled breath | | |
| | 13 VOCs: Isoprene, C16 hydrocarbon, 4,7-Dimethyl-undecane, 2,6-Dimethyl-heptane, 4-Methyl-octane, Hexadecane, 3,7-Dimethyl 1,3,6-octane, 2,4,6-Trimethyl-decane, Hexanal, Benzonitrile, Octadecane, Undecane, Terpineol | Predictive Profile | eNose, chemical sensor |
| Chemical Markers | | | |
| Nitric Oxide | During inflammation, larger amount of NO are produced for prolonged periods. NO concentrations are known to be higher in disease such as asthma and COPD. | Increase | Chemical Sensor |
| CRP | Nonspecific marker of inflammation, has an inverse relation with lung function and probably reflects disease severity. CRP levels rise during exacerbations particularly when there is an increased neutrophilic influx due to abacterial cause. Also, a raised CRP in stable state predicts recurrent exacerbations either due to a failure to completely resolve the first episode or an underlying airway colonization that predisposes to further episodes | Increase | Chemical Sensor |
| External Index | | | |
| Air Temperature | Cold temperatures increase risk of exacerbation | Risk factor/Trigger | Integrated weather application to sync with devices to shown when someone is more at risk Ambient air sensor |
| Air Contaminants | Increase in known allergens for patients increases risk of an exacerbation Real-time monitoring of personal air pollution exposure | Risk factor/Trigger Increase in particulate count/size --> increase in AECOPD | |

TABLE 1-continued

Physiological markers for the respiratory distress.

| Measurement | Physiology/ Additional Notes | Response to Acute Exacerbation | Exemplary Method of Measurement/Devices |
|---|---|---|---|
| | Can monitor number of particulates and their size- can inform predictions of acute exacerbations or have more long-term monitoring benefits | | |
| Humidity | cold dry air is a trigger for asthma attacked | Risk factor/Trigger | |
| Altitude | Fewer exacerbations occur at high altitudes | Risk factor/Trigger | |
| Air Pressure | Fewer exacerbations occur at low pressure | Risk factor/Trigger | |

What is claimed is:

1. A system for monitoring and treating respiratory distress in a patient, comprising:
   a portable device including:
      a signal input configured to receive patient condition signals indicative of autonomic balance of the patient;
      a signal processing circuit configured to process the patient condition signals and to generate patient condition parameters using the processed patient condition signals, the patient condition parameters indicative of the autonomic balance of the patient; and
      a respiratory distress analyzer configured to determine a state of the respiratory distress using the patient condition parameters, the respiratory distress analyzer including a parameter analysis circuit configured to analyze the patient condition parameters for a degree of autonomic imbalance of the patient and to determine a quantitative measure of the state of the respiratory distress using an outcome of the analysis; and
   implantable and non-implantable sensors each configured to be communicatively coupled to the portable device and to sense a patient condition signal of the patient condition signals.

2. The system of claim 1, further comprising:
   an implantable therapy device configured to deliver one or more therapies treating the respiratory distress, the implantable therapy device including a neuromodulation device; and
   a control circuit configured to control the delivery of the one or more therapies using the quantitative measure of the state of the respiratory distress.

3. The system of claim 1, wherein the parameter analysis circuit is configured to determine a patient condition metric being a linear or nonlinear combination of the patient condition parameters and to perform at least one of prediction or detection of an exacerbation of the respiratory distress based on the patient condition metric, and the respiratory distress analyzer further comprises a notification circuit configured to produce an alert notifying a result of the performance of the at least one of prediction and detection.

4. The system of claim 3, wherein the signal processing circuit is configured to generate patient condition parameters indicative of one or more physiological markers of asthma, the parameter analysis circuit is configured to perform at least one of prediction or detection of an asthma attack, and the notification circuit is configured to produce an asthma alert notifying at least one of the asthma attack being predicted or the asthma attack being detected.

5. The system of claim 3, wherein the signal processing circuit is configured to generate patient condition parameters indicative of one or more physiological markers of chronic obstructive pulmonary disease (COPD), the parameter analysis circuit is configured to perform at least one of prediction or detection of an exacerbation of COPD, and the notification circuit is configured to produce a COPD alert notifying at least one of the exacerbation of COPD being predicted or the exacerbation of COPD being detected.

6. The system of claim 1, further comprising:
   a signal processing controller configured to receive a processing control signal and adjust the processing of the patient condition signals based on the processing control signal; and
   a signal processing sensor configured to sense a physical state of the patient and to produce the processing control signal based on the physical state.

7. The system of claim 1, wherein the signal input are configured to receive one or more respiratory signals indicative of respiratory cycles including inspiratory and expiratory phases and one or more cardiac signals indicative of cardiac cycles including at least ventricular depolarizations, the signal processing circuit is configured to process the one or more respiratory signals and the one or more cardiac signals and to generate one or more respiration-mediated physiological parameters of the patient condition parameters, and the parameter analysis circuit is configured to determine the state of the respiratory distress based on at least the one or more respiration-mediated physiological parameters.

8. The system of claim 7, wherein the signal processing circuit is configured to generate one or more respiration sinus arrhythmia (RSA) parameters of the one or more respiration-mediated physiological parameters, the one or more RSA parameters being one or more measures of the RSA, and the parameter analysis circuit is configured to determine the state of the respiratory distress based on at least the one or more RSA parameters.

9. The system of claim 1, wherein the signal input are configured to receive one or more blood pressure signals indicative of blood pressure, one or more cardiac signals indicative of cardiac cycles including at least ventricular depolarizations, and one or more physical state signals indicative of a physical state of the patient, the signal processing circuit is configured to process the one or more blood pressure signals, the one or more cardiac signals, and the one or more physical state signals and to generate one or more baroreflex sensitivity (BRS) parameters of the patient condition parameters, the one or more BRS parameters being one or more measures of the BRS, and the parameter analysis circuit is configured to determine the state of the respiratory distress based on at least the one or more BRS parameters.

10. The system of claim 9, wherein the signal processing circuit is configured to detect levels of physical activity or exertion of the patient from the one or more physical state signals and to generate the one or more BRS parameters each for a plurality of levels of the physical activity or exertion.

11. The system of claim 9, wherein the signal processing circuit is configured to detect a type of posture change of the patient from the one or more physical state signals and to stratify the one or more BRS parameters by the detected type of posture change.

12. The system of claim 11, wherein the signal processing circuit is configured to detect one or more of a magnitude or a duration of posture change of the patient from the one or more physical state signals and to stratify the one or more BRS parameters by the detected one or more of the magnitude or the duration of posture change.

13. A method for monitoring and treating respiratory distress in a patient, comprising:
receiving patient condition signals indicative of autonomic balance of the patient from an implantable sensor placed in the patient and a non-implantable sensor worn by the patient; and
monitoring the state of the respiratory distress automatically using a portable device communicatively coupled to each of the implantable sensor and the non-implantable sensor, the monitoring including:
processing the patient condition signals;
generating patient condition parameters using the processed patient condition signals, the patient condition parameters indicative of the autonomic balance of the patient;
analyzing the patient condition parameters for a degree of autonomic imbalance of the patient using the patient condition parameters; and
determining a quantitative measure of the state of the respiratory distress using an outcome of the analysis.

14. The method of claim 13, further comprising:
delivering one or more therapies treating the respiratory distress using an implantable therapy device including at least a neuromodulation device; and
controlling the delivery of the one or more therapies using the quantitative measure of the state of the respiratory distress using a control circuit of the implantable therapy device.

15. The method of claim 13, further comprising:
determining a patient condition metric being a linear or nonlinear combination of the patient condition parameters;
performing at least one of prediction or detection of an exacerbation of the respiratory distress based on the patient condition metric; and
producing an alert notifying a result of the performance of the at least one of prediction and detection.

16. The method of claim 13, further comprising:
sensing a physical state of the patient; and
adjusting the processing of the patient condition signals based on the sensed physical state.

17. The method of claim 13, wherein the receiving patient condition signals comprises receiving one or more respiratory signals indicative of respiratory cycles including inspiratory and expiratory phases and one or more cardiac signals indicative of cardiac cycles including at least ventricular depolarizations, and generating the patient condition parameters comprises generating one or more respiration-mediated physiological parameters of the patient condition parameters.

18. The method of claim 17, wherein generating the one or more respiration-mediated physiological parameters comprises generating one or more respiration sinus arrhythmia (RSA) parameters being one or more measures of the RSA.

19. The method of claim 13, wherein the receiving patient condition signals comprises receiving one or more blood pressure signals indicative of blood pressure, one or more cardiac signals indicative of cardiac cycles including at least ventricular depolarizations, and one or more physical state signals indicative of a physical state of the patient, and generating the patient condition parameters comprises generating one or more baroreflex sensitivity (BRS) parameters being one or more measures of the BRS.

20. The method of claim 19, wherein generating the patient condition parameters comprises one or more of:
detecting levels of physical activity or exertion of the patient from the one or more physical state signals and generating the one or more BRS parameters each for a plurality of levels of the physical activity or exertion;
detecting a type of posture change of the patient from the one or more physical state signals and stratifying the one or more BRS parameters by the detected type of posture change;
detecting a magnitude or a duration of posture change of the patient from the one or more physical state signals and stratifying the one or more BRS parameters by the detected magnitude of posture change; or
detecting a duration of posture change of the patient from the one or more physical state signals and stratifying the one or more BRS parameters by the detected duration of posture change.

* * * * *